US012642516B2

(12) United States Patent
Zhang et al.

(10) Patent No.: US 12,642,516 B2
(45) Date of Patent: Jun. 2, 2026

(54) CLIP INSTRUMENTS

(71) Applicant: HANGZHOU AGS MEDTECH CO., LTD., Hangzhou (CN)

(72) Inventors: Cheng Zhang, Hangzhou (CN); Baiming Shi, Hangzhou (CN)

(73) Assignee: HANGZHOU AGS MEDTECH CO., LTD., Hangzhou (CN)

( * ) Notice: Subject to any disclaimer, the term of this patent is extended or adjusted under 35 U.S.C. 154(b) by 49 days.

(21) Appl. No.: 18/613,048

(22) Filed: Mar. 21, 2024

(65) Prior Publication Data

US 2024/0225629 A1     Jul. 11, 2024

Related U.S. Application Data

(63) Continuation of application No. PCT/CN2022/122089, filed on Sep. 28, 2022.

(30) Foreign Application Priority Data

Sep. 30, 2021     (CN) .......................... 202111162631.X
Nov. 11, 2021     (CN) .......................... 202111334658.2

(51) Int. Cl.
A61B 17/00          (2006.01)
(52) U.S. Cl.
CPC .... A61B 17/0057 (2013.01); A61B 17/00234 (2013.01); *A61B 2017/00296* (2013.01); *A61B 2017/00584* (2013.01); *A61B 2017/00623* (2013.01)
(58) Field of Classification Search
CPC .......... A61B 17/0057; A61B 17/00234; A61B 2017/00584; A61B 17/083; A61B 17/10

USPC ........................................................ 251/7, 9
See application file for complete search history.

(56) References Cited

U.S. PATENT DOCUMENTS

| | | | |
|---|---|---|---|
| 2,256,382 | A | 9/1941 | Dole |
| 4,296,751 | A | 10/1981 | Blake, III et al. |
| 4,556,058 | A | 12/1985 | Green |
| 4,612,932 | A | 9/1986 | Caspar et al. |

(Continued)

FOREIGN PATENT DOCUMENTS

| | | |
|---|---|---|
| CN | 203328756 U | 12/2013 |
| CN | 109788958 A | 5/2019 |

(Continued)

OTHER PUBLICATIONS

International Search Report in PCT/CN2022/122089 mailed on Dec. 21, 2022, 8 pages.

(Continued)

*Primary Examiner* — Julian W Woo
(74) *Attorney, Agent, or Firm* — METIS IP LLC

(57) ABSTRACT

A clip instrument may include a clip arm and a locking part. The clip arm may include at least two clips for clamping at least one tissue and at least two extending parts releasably connected to the at least two clips, respectively. The clip arm has an open state and a closed state, wherein the at least two clips are spaced apart from each other when the clip arm is in the open state to form a space for clamping the at least one tissue, and the at least two clips are close to each other when the clip arm is in the closed state. The locking part may be configured to lock two clips of the at least two clips when a distance between the two clips is less than a preset distance.

17 Claims, 23 Drawing Sheets

(56) References Cited

U.S. PATENT DOCUMENTS

| | | | |
|---|---|---|---|
| 4,671,278 A | 6/1987 | Chin | |
| 5,192,288 A | 3/1993 | Thompson et al. | |
| 5,464,416 A * | 11/1995 | Steckel | A61B 17/1285 |
| | | | 606/158 |
| 5,779,720 A | 7/1998 | Walder-Utz et al. | |
| 6,719,767 B1 | 4/2004 | Kimblad | |
| 7,011,667 B2 | 3/2006 | Kobayashi et al. | |
| 7,011,669 B2 | 3/2006 | Kimblad | |
| 7,223,271 B2 | 5/2007 | Muramatsu et al. | |
| 7,879,052 B2 * | 2/2011 | Adams | A61B 17/122 |
| | | | 606/157 |
| 8,523,880 B2 | 9/2013 | Kissel et al. | |
| 10,188,383 B2 | 1/2019 | Miraki et al. | |
| 10,729,448 B2 * | 8/2020 | Patel | A61B 17/122 |
| 10,820,903 B2 | 11/2020 | Randhawa et al. | |
| 11,071,552 B2 | 7/2021 | Saenz Villalobos et al. | |
| 11,123,064 B2 | 9/2021 | Chen et al. | |
| 11,369,386 B2 | 6/2022 | Wallace | |
| 11,583,293 B2 * | 2/2023 | Menn | A61B 17/1285 |
| 11,992,223 B2 * | 5/2024 | Muyari | A61B 17/122 |
| 12,465,369 B2 * | 11/2025 | Tsuji | A61B 17/1285 |
| 2002/0128667 A1 | 9/2002 | Kobayashi et al. | |
| 2002/0151916 A1 | 10/2002 | Muramatsu et al. | |
| 2003/0153946 A1 | 8/2003 | Kimblad | |
| 2004/0204724 A1 | 10/2004 | Kissel et al. | |
| 2004/0249414 A1 | 12/2004 | Kissel et al. | |
| 2005/0216036 A1 | 9/2005 | Nakao | |
| 2009/0318937 A1 | 12/2009 | Matsuoka et al. | |
| 2014/0316440 A1 | 10/2014 | Gordon | |
| 2016/0183937 A1 | 6/2016 | Miraki et al. | |
| 2019/0167265 A1 | 6/2019 | Chen et al. | |
| 2020/0008811 A1 | 1/2020 | Itoh et al. | |
| 2020/0405317 A1 | 12/2020 | Wallace | |
| 2022/0386856 A1 | 12/2022 | Shi et al. | |
| 2023/0172616 A1 | 6/2023 | Goldenberg et al. | |
| 2024/0398423 A1 | 12/2024 | Shi | |

FOREIGN PATENT DOCUMENTS

| | | |
|---|---|---|
| CN | 110393564 A | 11/2019 |
| CN | 211270957 U | 8/2020 |
| CN | 211355689 U | 8/2020 |
| CN | 111655172 A | 9/2020 |
| CN | 212490043 U | 2/2021 |
| CN | 213406175 U | 6/2021 |
| JP | 2006087537 A | 4/2006 |
| JP | 5383222 B2 | 8/2010 |
| JP | 2014188344 A | 10/2014 |
| WO | 2015000561 A1 | 1/2015 |

OTHER PUBLICATIONS

Written Opinion in PCT/CN2022/122089 mailed on Dec. 21, 2022, 7 pages.

International Search Report in PCT/CN2022/119233 mailed on Dec. 13, 2022, 8 pages.

Written Opinion in PCT/CN2022/119233 mailed on Dec. 13, 2022, 9 pages.

Partial Supplementary European Search Report in European Application No. 22869378.4 mailed on Nov. 26, 2024, 14 pages.

* cited by examiner

500

500A

510

520

500B

500

500A

510

520

500B

500

500A

520

510

500B

<u>310</u>

<u>310</u>

<u>310</u>

440

400

440

400

440

400

440—

400

440—

400

440—

400

CLIP INSTRUMENTS

CROSS-REFERENCE TO RELATED APPLICATIONS

This application is a continuation of International Patent Application No. PCT/CN2022/122089, filed on Sep. 28, 2022, which claims priority of Chinese Patent Application No. 202111162631.X, filed on Sep. 30, 2021 and Chinese Patent Application No. 202111334658.2, filed on Nov. 11, 2021, the entire contents of each of which are hereby incorporated by reference.

TECHNICAL FIELD

The present disclosure relates to the field of medical instruments, and in particular, to clip instruments.

BACKGROUND

Endoscopes have been around for more than 50 years and have gone through stages from disease diagnosis to disease treatment. The endoscopes are effective and reliable in the treatment of some diseases. Flexible endoscopes have been widely used in the fields of gastroenterology, gynecology, urology, respiratory, and cardiovascular due to their characteristics of non-surgical laparotomy and minimal invasion. Simultaneously, technical requirements for the combination of miniaturization, maneuverability, and high flexibility are raised for surgical instruments used with the flexible endoscopes. Biological organs such as the stomach and intestines are prone to bleeding, mucosal damage, or even perforation due to various diseases, accidents, or injuries during endoscopic diagnosis and treatment. In clinic, bleeding can be controlled mechanically through a clip instrument. The clip instrument can grasp the surrounding tissue(s) of a wound and temporarily hold wound edges together to close the wound. The clip instrument can also be used in wound suturing.

SUMMARY

Some embodiments of the present disclosure provide a clip instrument. The clip instrument may include a clip arm and a locking part. The clip arm may include at least two clips for clamping at least one tissue and at least two extending parts releasably connected to the at least two clips, respectively. The clip arm may have an open state and a closed state. The at least two clips may be spaced apart from each other when the clip arm is in the open state, and the at least two clips may be close to each other when the clip arm is in the closed state. The locking part may be disposed on the at least two clips. The locking part may be configured to lock two clips of the at least two clips when a distance between the two clips is less than a preset distance.

According to some embodiments of the present disclosure, by disposing the locking part on the at least two clips, the clip arm can be maintained in the closed state within a body (e.g., a human body), thereby improving a clamping effectiveness of the clip arm. By releasably connecting the at least two clips to the at least two extending parts, respectively, the at least two extending parts and a conveying part that are not in contact with the at least one tissue can be removed from the body, and the at least two clips with a relatively small size can be left in the body, which can provide a relatively large operational space for subsequent surgical operation(s) and reduce an impact on the body.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

Figure 1:
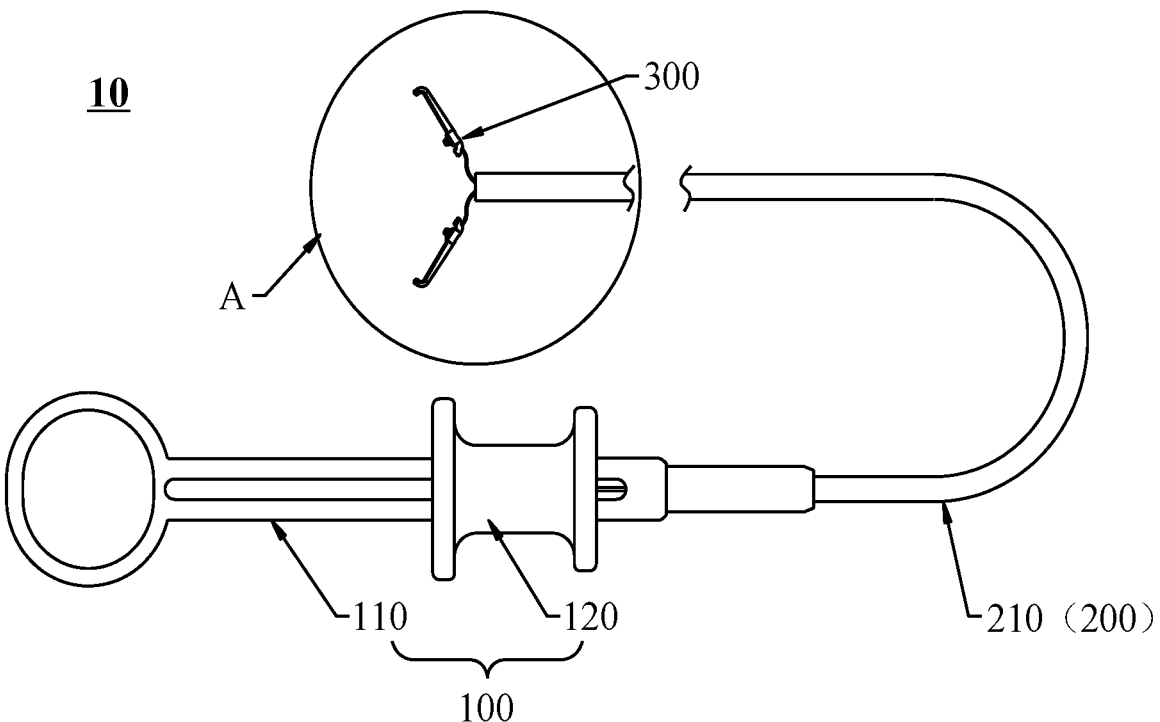
FIG. 1 is a schematic diagram illustrating an exemplary structure of a clip instrument according to some embodiments of the present disclosure.

In the drawings, 10 represents a clip instrument, 100 represents a control part, 110 represents a fixed handle, 120 represents a sliding handle, 200 represents a conveying part, 210 represents a sheath tube, 211 represents a first sheath, 212 represents a second sheath, 213 represents an outer tube, 214 represents an inner tube, 215 represents a first connecting structure, 216 represents a second connecting structure, 220 represents a core shaft, 230 represents a resisting part, 240 represents a groove, 250 represents a second external connecting part, 300 represents a clip arm, 310 represents at least one clip, 310A represents a first clip, 310B represents a second clip, 311 represents a first connecting part, 312 represents a through-hole, 313 represents a limiting channel, 314 represents a locked part, 320 represents a resisted part, 400 represents at least one extending part, 400A represents a first extending part, 400B represents a second extending part, 410 represents a distal coupling part, 420 represents a bending part, 430 represents a proximal coupling part, 440 represents a second connecting part, 441 represents a limiting protrusion, 500 represents at least one locking part, 500A represents a first locking part, 500B represents a second locking part, 510 represents a locking protrusion, 520 represents a locking recess, 530 represents a locking channel, 540 represents a first external connecting part, 541 represents a connecting groove, 542 represents an opening, and 20 represents at least one tissue.

DETAILED DESCRIPTION

In order to further illustrate the technical solutions of the embodiments of the present disclosure, a brief introduction will be made to the drawings required for the description of the embodiments. It is obvious that the drawings described below are only examples or embodiments of the present disclosure. For those skilled in the art, without exercising inventive labor, the present disclosure may also be applied to other similar scenarios based on these drawings. Unless otherwise indicated or specified from the context, identical reference numerals in the drawings represent identical structures or operations.

As shown in the present disclosure and the claims, unless otherwise clearly indicated by the context, terms such as "one," "a," "an," and/or "the" are not specifically limited to singular forms and may also include plural forms. Generally, the terms "comprise," "comprises," "comprising," "include," "includes," and "including" only indicate the presence of the explicitly identified operations and elements, and these operations and elements do not constitute an exclusive listing. Methods or devices may also include other operations or elements.

FIG. 1 is a schematic diagram illustrating an exemplary structure of a clip instrument 10 according to some embodiments of the present disclosure.

As shown in FIG. 1, in some embodiments, the clip instrument 10 may include a control part 100, a conveying part 200, and a clip arm 300. The control part 100 may be disposed at a distal end of the conveying part 200, and the clip arm 300 may be disposed at a proximal end of the conveying part 200. The terms "proximal end" and "distal end" in some embodiments of the present disclosure may represent directions. For example, the "proximal end" refers to a side facing an operator along an axial direction of the clip instrument 10 (e.g., an extension direction of a sheath tube 210 of the conveying part 200 within an endoscopic channel), and the "distal end" refers to a side entering a body for treatment along the axial direction of the clip instrument 10. Correspondingly, a direction from the distal end to the proximal end refers to an axial direction of the clip instrument 10 (e.g., the sheath tube 210, the conveying part 200, or other components of the clip instrument 10) from the side entering the body for treatment to the side facing the operator. The terms "proximal end" and "distal end" may also represent partial structures located in the corresponding directions, and should not be understood to only represent the ends.

In some application scenarios, the conveying part 200 may have a good passability. The conveying part 200 and the clip arm 300 at the distal end of the conveying part 200 may enter the body through an operational channel of an endoscope to approach at least one tissue 20 to be clamped. The at least one tissue 20 refers to organ tissue(s) 20 of a human body or other organisms. The control part 100 may be located outside the human body or other organisms, and the operator may control the clip arm 300 for surgical operations by manipulating the control part 100. For example, the clip arm 300 may clamp a wound of the at least one tissue 20 to keep the wound closed, facilitating wound healing.

Figure 7:
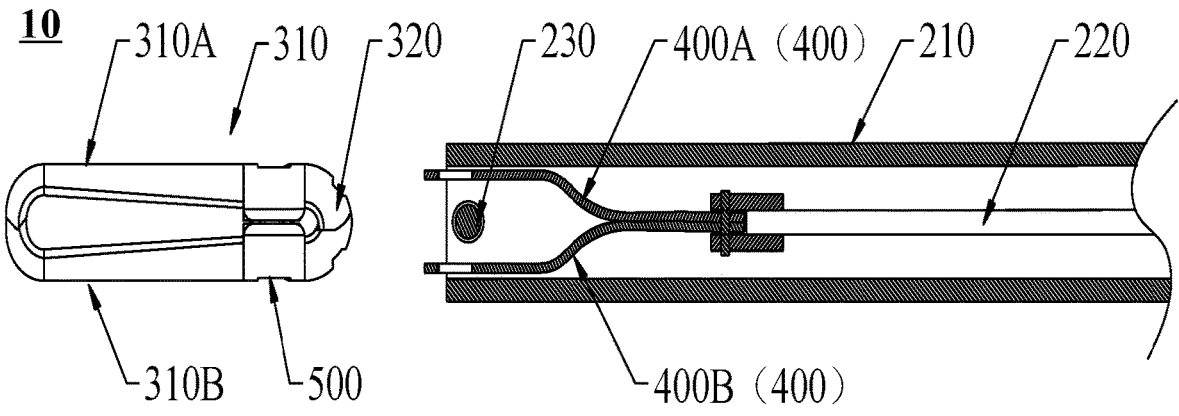
FIG. 7 is a schematic diagram illustrating an exemplary releasing structure of at least two clips and a sheath tube according to some embodiments of the present disclosure, wherein the sheath tube is shown in an axial section view.

In some embodiments, the conveying part 200 may include the sheath tube 210 disposed with a channel and a core shaft 220 (as shown in FIG. 7) extending along an axial direction within the channel of the sheath tube 210. A proximal end of the core shaft 220 may be connected to the control part 100, and a distal end of the core shaft 220 may be connected to the clip arm 300. The terms "axial" and "radial" in some embodiments of the present disclosure may represent directions. For example, the "radial" direction may be perpendicular to the "axial" direction. Alternatively, the axial direction refers to as an extension direction of the channel of the sheath tube 210 (also referred to as the extension direction of the sheath tube 210), and the radial direction refers to as a direction perpendicular to the extension direction of the channel of the sheath tube 210.

In some embodiments, the sheath tube 210 may have flexibility, so as to be bent in any direction. In some embodiments, the control part 100 may include a fixed handle 110 and a sliding handle 120. The sliding handle 120 may slide axially with respect to the fixed handle 110. A distal end of the sliding handle 120 may be fixedly connected to the proximal end of the core shaft 220. The operator may control an axial movement of the core shaft 220 within the channel of the sheath tube 210 by controlling the sliding handle 120 along an axial direction of the fixed handle 110 outside the body, thereby causing the clip arm 300 to perform the corresponding surgical operations.

Embodiment One of the present disclosure provides an exemplary clip instrument 10, which is described in detail below in combination with FIGS. 2A to 18B.

Figure 2A:
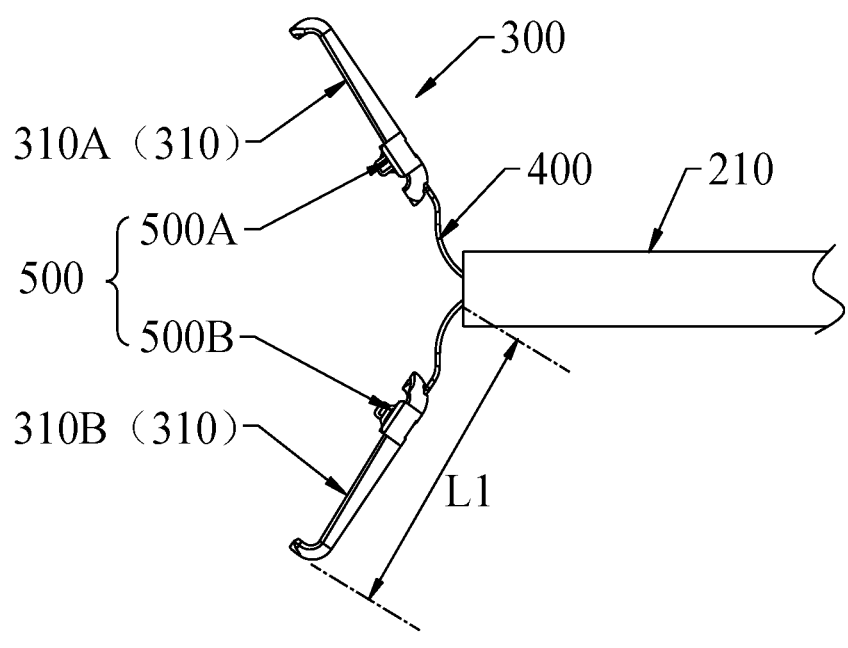
FIG. 2A is a partial enlarged view of a region A of the clip instrument shown in FIG. 1, wherein a clip arm of the clip instrument is in an open state.
Figure 2B:
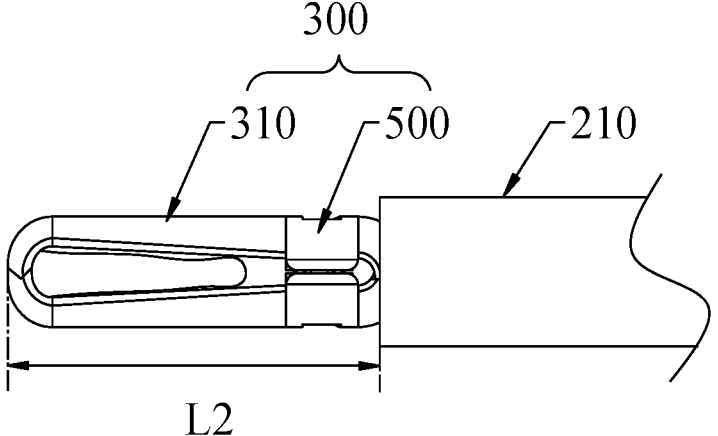
FIG. 2B is a partial enlarged view of a region A of the clip instrument shown in FIG. 1, wherein a clip arm of the clip instrument is in a closed state.

FIG. 2A is a partial enlarged view of a region A of the clip instrument 10 shown in FIG. 1, wherein the clip arm 300 of the clip instrument 10 is in an open state. FIG. 2B is a partial enlarged view of a region A of the clip instrument 10 shown in FIG. 1, wherein the clip arm 300 of the clip instrument 10 is in a closed state.

As shown in FIGS. 2A and 2B, in some embodiments, the clip arm 300 may include at least two clips 310 for clamping at least one tissue 20. A clamping space may be formed between the at least two clips 310. The clip arm 300 may have the open state and the closed state. The at least two clips 310 may be spaced apart from each other when the clip arm 300 is in the open state, and the at least two clips 310 may be close to each other when the clip arm 300 is in the closed state.

In some embodiments, the clip arm 300 may further include a locking part 500. The locking part 500 may be disposed on the at least two clips 310. The locking part 500 may be configured to lock two clips 310 of the at least two clips 310 when a distance between the two clips 310 is less than a preset distance, thereby maintaining the two clips 310 in a closed state. After the locking part 500 locks the two clips 310, the two clips 310 may maintain the closed state under external disturbances with a force less than a preset force value. At this time, the at least two clips 310 and/or the locking part 500 may be in a locked state. By disposing the locking part 500 on the at least two clips 310, the at least two clips 310 can be maintained in the closed state within the body, thereby improving a clamping effectiveness of the at least two clips 310. It should be noted that an open state and/or the closed state of the at least two clips 310 are the same as the open state and/or the closed state of the clip arm 300, respectively.

In some embodiments, the at least two clips 310 may include a first clip 310A and a second clip 310B. In some embodiments, the locking part 500 may include a first locking part 500A disposed on the first clip 310A and a second locking part 500B disposed on the second clip 310B. The first locking part 500A and the second locking part 500B may cooperate with each other to form a lock. In some embodiments, the first locking part 500A may be disposed at a distal end, a middle, a proximal end, or any other positions of the first clip 310A, and the second locking part 500B may be disposed on the second clip 310B at a position corresponding to the position of the first locking part 500A.

The locking part 500 may have an unlocked state and a locked state. The first locking part 500A and the second locking part 500B may separate from each other when the locking part 500 is in the unlocked state. The first locking part 500A and the second locking part 500B may cooperate with each other to lock the first clip 310A and the second clip 310B when the locking part 500 is in the locked state.

In some embodiments, the clip arm 300 may further include at least two extending parts 400 releasably connected to the at least two clips 310, respectively. Proximal ends of the at least two extending parts 400 may be connected to the core shaft 220 (not shown in FIGS. 2A and 2B), and distal ends of the at least two extending parts 400 may be releasably connected to the at least two clips 310, respectively. The "releasably connected" in some embodiments of the present disclosure refers to that two components maintain a connection state when a preset condition is satisfied (e.g., when an external force is less than a preset threshold), and two components release from each other when the preset condition is not satisfied (e.g., when the external force is larger than the preset threshold). When the at least two clips 310 are in the open state, distal ends of the first clip 310A and the second clip 310B may be separated from each other, and the at least two extending parts 400 may cause proximal ends of the first clip 310A and the second clip 310B to be separated from each other, thereby providing sufficient span for the at least two clips 310 to clamp the at least one tissue 20. When the at least two clips 310 are locked, the distal ends of the first clip 310A and the second clip 310B may abut against each other (or abut against the tissue being clamped) to be closed, and the proximal ends of the first clip 310A and the second clip 310B may also abut against each other to be closed. In some embodiments, after the at least two clips 310 are locked, the at least two extending parts 400 may be released from the at least two clips 310, the at least two extending parts 400 and the conveying part 200 may be removed from an endoscopic channel, and the at least two clips 310 and the locking part 500 may remain inside the body. By releasably connecting the at least two clips 310 to the at least two extending parts 400, respectively, the at least two extending parts 400 and the conveying part 200 that are not in contact with the at least one tissue 20 can be removed from the body, and the at least two clips 310 with a relatively small size can be left in the body, which can provide a relatively large operational space for subsequent surgical operation(s) and reduce an impact on the body.

In some embodiments, the core shaft 220 may move axially within the sheath tube 210, so as to drive the at least two extending parts 400 to move axially with respect to the sheath tube 210. The axial movement of the at least two extending parts 400 may drive the at least two clips 310 (or the clip arm 300) to switch between the open state and the closed state, thereby clamping the at least one tissue 20.

In some embodiments, the proximal ends of the at least two extending parts 400 may be disposed within the sheath tube 210 and connected to the core shaft 220. In some embodiments, each of the at least two extending parts 400 may include a bending part (e.g., a bending part 420) with a curved shape. The bending parts may move into or out of the sheath tube 210. During the movement of the bending parts into or out of the sheath tube 210, due to the limitation of a size of the sheath tube 210, the bending parts may deform under a radial force of the sheath tube 210, thereby causing the two clips 310 at the distal end of the at least two extending parts 400 to move closer to each other or farther from each other and changing the distance between the two clips 310. By setting a structure or a locking mode of the locking part 500 based on clamping requirement(s) of the clip instrument 10, the first locking part 500A and the second locking part 500B may cooperate with each other to lock the two clips 310 when the distance between the two clips 310 is less than the preset distance. In some embodiments, the distance between the two clips 310 being less than the preset distance refers to that a distance between a first region where the first locking part 500A is disposed on the first clip 310A and a second region where the second locking part 500B is disposed on the second clip 310B is less than the preset distance. In other words, when the core shaft 220 moves to the proximal end within the sheath tube 210 to drive the bending part of each of the at least two extending parts 400 into the sheath tube 210, the bending parts may deform under the action of the sheath tube 210 to drive the two clips 310 closer to each other until the distance between the first region on the first clip 310A and the second region on the second clip 310B is less than the preset distance. At this point, the first locking part 500A disposed on the first clip 310A and the second locking part 500B disposed on the second clip 310B may be locked, and the first clip 310A and the second clip 310B (or the clip arm 300) may be locked. It should be noted that the preset distance may be determined according to a size of a target to be clamped, and a specific value of the preset distance may not be limited in some embodiments of the present disclosure.

In some embodiments, a first length L1 of the clip arm 300 outside the sheath tube 210 in the open state may be larger than a second length L2 outside the sheath tube 210 in the closed state. In some embodiments, when the clip arm 300 is in the open state, at least a portion of the at least two extending parts 400 may protrude from the sheath tube 210 to increase the first length L1 of the clip arm 300 outside the sheath tube 210, thereby increasing the span between the at least two clips 310 to clamp the at least one tissue 20. When the clip arm 300 is in the closed state, at least a portion of the at least two extending parts 400 may retract into the sheath tube 210 to reduce the second length L2 of the clip arm 300 outside the sheath tube 210, thereby reducing a size of the at least two clips 310 retained inside the body and minimizing the impact on the body.

In some embodiments, the first length L1 may be within a range from 4 millimeters to 40 millimeters. In some embodiments, the first length L1 may be within a range from 3.5 millimeters to 43 millimeters. In some embodiments, the first length L1 may be within a range from 3 millimeters to 45 millimeters. In some embodiments, the first length L1 may be within a range from 5 millimeters to 35 millimeters. In some embodiments, the second length L2 may be within a range from 3 millimeters to 20 millimeters. In some embodiments, the second length L2 may be within a range from 2.5 millimeters to 23 millimeters. In some embodiments, the second length L2 may be within a range from 2 millimeters to 25 millimeters. In some embodiments, the second length L2 may be within a range from 4 millimeters to 15 millimeters. In some embodiments, a ratio of the first length L1 to the second length L2 may be 2:1. In some embodiments, the ratio of the first length L1 to the second length L2 may be 5:1. In some embodiments, the ratio of the first length L1 to the second length L2 may be 1.5:1.

Figure 3:
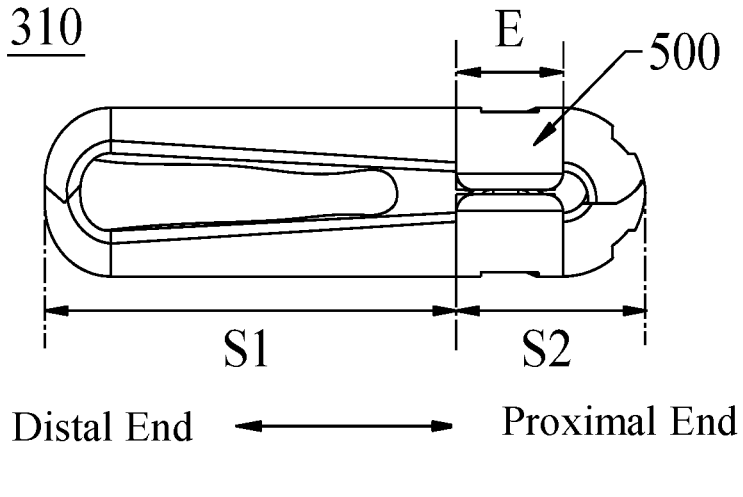
FIG. 3 is a schematic diagram illustrating an exemplary structure of at least two clips and a locking part according to some embodiments of the present disclosure, wherein a clip arm is in an open state.

FIG. 3 is a schematic diagram illustrating an exemplary structure of at least two clips 310 and a locking part 500 according to some embodiments of the present disclosure, wherein a clip arm 300 is in an open state.

As shown in FIG. 3, in some embodiments, a length of one of the at least two clips 310 (also referred to as a clip 310) along an extension direction may be within a range from 3 millimeters to 20 millimeters. In some embodiments, the length of the clip 310 along the extension direction may be within a range from 2.5 millimeters to 25 millimeters. In some embodiments, the length of the clip 310 along the extension direction may be within a range from 5 millimeters to 15 millimeters. In some embodiments, the length of the clip 310 along the extension direction may be the same as the second length L2 when the clip arm 300 is in the closed state. That is, when the clip arm 300 is in the closed state, only the at least two clips 310 may extend outside the sheath tube 210.

In some embodiments, the locking part 500 may be disposed at a position between a distal end and a proximal end of the clip 310. In some embodiments, the locking part 500 may be disposed at a position between a midpoint and the proximal end of the clip 310. In some embodiments, a ratio of a distance S1 between a distal end of the locking part 500 and the distal end of the clip 310 to a distance S2 between the distal end of the locking part 500 and the proximal end of the clip 310 may be larger than 1. In some embodiments, the ratio of the distance S1 between the distal end of the locking part 500 and the distal end of the clip 310 to the distance S2 between the distal end of the locking part 500 and the proximal end of the clip 310 may be 2:1. By disposing the locking part 500 at a position closer to the proximal end of the clip 310, a clamping space at the distal end of the clip 310 for accommodating the at least one tissue 20 can be improved. Further, the position of the locking part 500 can be away from a position where the at least one tissue 20 is located, which can avoid affecting the coordination of the locking part 500.

In some embodiments, the locking part 500 may be disposed at a position between the midpoint and the distal end of the clip 310.

In some embodiments, in order to avoid distal separation of the at least two clips 310 after locking and maintain the stability of the closed state of the at least two clips 310, the locking part 500 may have a locking length along the extension direction of the clip 310. The locking length refers to a size of the locking part 500 locked along the extension direction of the clip 310. In some embodiments, the locking length E of the locking part 500 along the extension direction of the clip 310 may not be less than 1 millimeter. In some embodiments, the locking length E of the locking part 500 along the extension direction of the clip 310 may not be less than 0.5 millimeters. In some embodiments, the locking length E of the locking part 500 along the extension direction of the clip 310 may not be less than 2 millimeters.

In some embodiments, in order to avoid the distal separation of the at least two clips 310 after locking and maintain the stability of the closed state of the at least two clips 310, both the proximal ends and the distal ends of the at least two clips 310 may be closed when the at least two clips 310 are in the closed state. In other words, when the at least two clips 310 are in the closed state, a distal end of the first clip 310A and a distal end of the second clip 310B may be in contact with each other, and a proximal end of the first clip 310A and a proximal end of the second clip 310B may be in contact with each other. It should be noted that when at least one tissue is clamped between the distal end of the first clip 310A and the distal end of the second clip 310B, the distal end of the first clip 310A and the distal end of the second clip 310B may not be completely closed. In this case, the closed state of the distal end of the first clip 310A and the distal end of the second clip 310B may include that structures (e.g., needles) at the distal end of the first clip 310A and the distal end of the second clip 310B contact with each other, or the distal end of the first clip 310A and the distal end of the second clip 310B exert a clamping force with a preset force value on the at least one tissue, or a distance between the distal end of the first clip 310A and the distal end of the second clip 310B is less than a preset distance (e.g., 1 millimeter, 0.5 millimeters, 0.2 millimeters, etc.). In some embodiments, by setting both the proximal ends and the distal ends of the at least two clips 310 to be closed when the at least two clips 310 are in the closed state, a locking stability of the at least two clips 310 in the closed state may be maintained without relying on the locking length of the locking part 500 (i.e., the locking length may be arbitrarily set). In some embodiments, the locking part 500 may have an arbitrary length. When the locking part 500 is locked, both the proximal ends and the distal ends of the at least two clips 310 may be closed. When there is a tendency for the distal ends of the at least two clips 310 to open, the proximal ends of the at least two clips 310 may have a tendency to approach each other with the locking part 500 as a fulcrum. The proximal ends of the at least two clips 310 may be already closed, which hinders the tendency to approach each other, thereby providing resistance to prevent the distal ends from opening. When there is a tendency for the proximal ends of the at least two clips 310 to open, the distal ends of the at least two clips 310 may have a tendency to approach each other with the locking part 500 as the fulcrum. The distal ends of the at least two clips 310 may be already closed, which hinders the tendency to approach each other, thereby providing resistance to prevent the proximal ends from opening.

It should be noted that the configuration that both the proximal ends and the distal ends of the at least two clips 310 are closed when the at least two clips 310 are in the closed state may be used separately from related configurations of the locking length of the locking part 500 in other embodiments. Each of the configurations can improve the locking stability of the at least two clips 310. In some other embodiments, the configuration that both the proximal ends and the distal ends of the at least two clips 310 are closed when the at least two clips 310 are in the closed state can also be used simultaneously with the related configurations of the locking length of the locking part 500 in other embodiments to maximize the reliability of the clip instrument 10.

Figure 4:
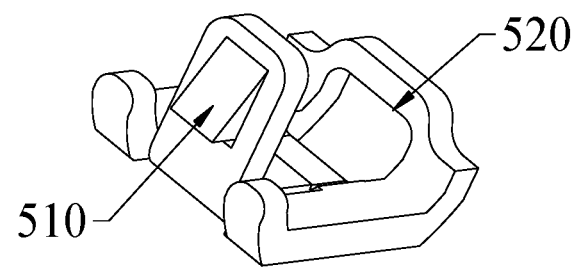
FIG. 4 is a schematic diagram illustrating an exemplary structure of a first locking part or a second locking part according to some embodiments of the present disclosure.

FIG. 4 is a schematic diagram illustrating an exemplary structure of a first locking part 500A or a second locking part 500B according to some embodiments of the present disclosure.

As shown in FIGS. 2A and 4, in some embodiments, the first locking part 500A may include at least one locking protrusion 510, and the second locking part 500B may include at least one locking recess 520. Each of the at least one locking protrusion 510 and one of the at least one locking recess 520 may cooperate with each other to lock the first clip 310A and the second clip 310B. In some embodiments, a structure of the first locking part 500A may be the same as a structure of the second locking part 500B. Each of the first locking part 500A and the second locking part 500B may include one locking protrusion 510 and one locking recess 520. The locking protrusion 510 of the first locking part 500A may cooperate with the locking recess 520 of the second locking part 500B, and the locking recess 520 of the first locking part 500A may cooperate with the locking protrusion 510 of the second locking part 500B, thereby locking the first clip 310A and the second clip 310B. In some embodiments, the structure of the first locking part 500A may be different from the structure of the second locking part 500B. The first locking part 500A may include one or more locking protrusions 510, and the second locking part 500B may include one or more locking recesses 520. The one or more locking protrusions 510 of the first locking part 500A may cooperate with the one or more locking recesses 520 of the second locking part 500B, respectively, to lock the first clip 310A and the second clip 310B.

As shown in FIG. 4, in some embodiments, a structure of the locking protrusion 510 may include a locking block, and a structure of the locking recess 520 may include a clamping slot. When the locking block and the clamping slot clamp, the first locking part 500A and the second locking part 500B may be locked. In some embodiments, one end of the locking block may be fixed to an outer surface of the first locking part 500A and/or the second locking part 500B, and another end protruding from the outer surface of the first locking part 500A and/or the second locking part 500B may form a free end. The clamping slot may be a structure (e.g., an opening, a groove, or other structures) on the first locking part 500A and/or the second locking part 500B capable of accommodating the locking block. The free end of the locking block may extend into the clamping slot and form a limiting clamp with an inner wall of the clamping slot. In some embodiments, the locking block and/or the clamping slot may have elasticity, so as to form a limiting cooperation through an extrusion deformation when the locking block and the clamping slot are closer to each other.

In some embodiments, structures of the locking protrusion 510 and the locking recess 520 may include other structural forms. For example, the structure of the locking protrusion 510 may be a limit buckle, and the structure of the locking recess 520 may be a clamping socket. More descriptions regarding the limit buckle and the clamping socket may be found in FIGS. 6A and 6B, and relative descriptions thereof.

Figure 5A:
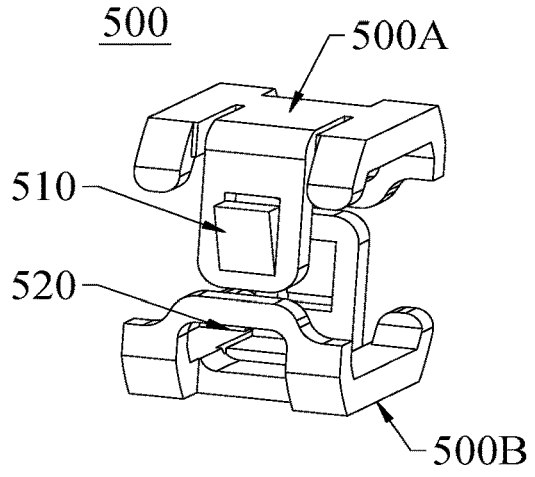
FIGS. 5A to 5C are schematic diagrams illustrating a matching process of a first locking part and a second locking part according to some embodiments of the present disclosure.
Figure 5B:
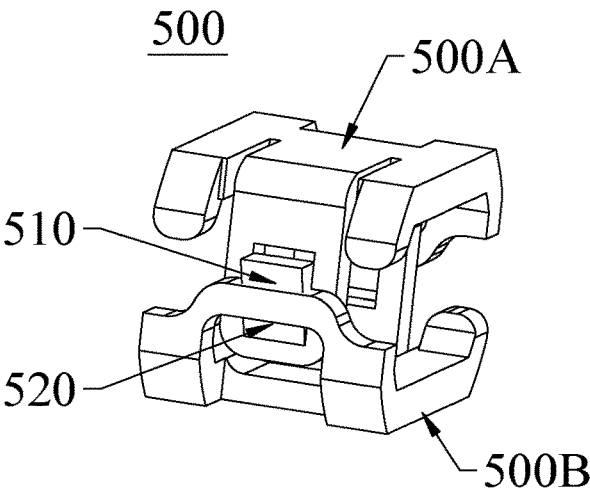
Figure 5C:
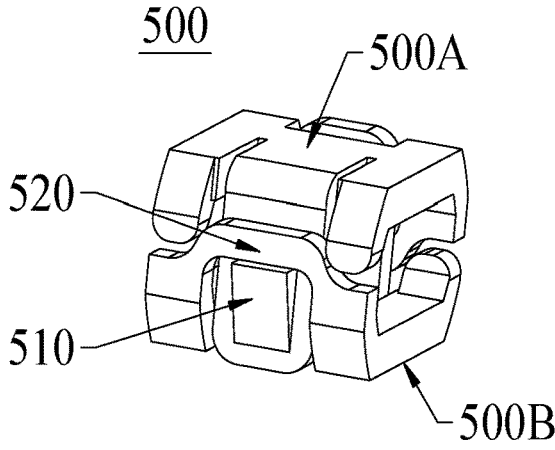

FIGS. 5A to 5C are schematic diagrams illustrating a matching process of a first locking part 500A and a second locking part 500B according to some embodiments of the present disclosure.

As shown in FIGS. 2A and 5A to 5C, in some embodiments, the locking part 500 and the at least two clips 310 may be separately formed to facilitate the separate processing of the locking part 500. The first locking part 500A and the first clip 310A may be separate structures, and the first locking part 500A may be detachably connected to the first clip 310A. For example, the first locking part 500A may be fixed to the first clip 310A through a manner such as a welding connection, an adhesive connection, a clamping connection, etc. The second locking part 500B and the second clip 310B may be separate structures, and the second locking part 500B may be detachably connected to the second clip 310B. For example, the second locking part 500B may be fixed to the second clip 310B through a manner such as a welding connection, an adhesive connection, a clamping connection, etc.

As shown in FIG. 5A, the first locking part 500A and the second locking part 500B are in a closed and unlocked state. The locking block of the locking protrusion 510 and the clamping slot of the locking recess 520 are close to each other, but the locking block has not extended into the clamping slot. As shown in FIG. 5B, the first locking part 500A and the second locking part 500B gradually approach each other, causing an extrusion deformation of the locking block and/or the clamping slot, such as a radially inward displacement of the locking block or a radially outward displacement of the clamping slot. As shown in FIG. 5C, the first locking part 500A and the second locking part 500B are in the locked state. As the first locking part 500A and the second locking part 500B continue to approach each other, after the clamping slot passes over the free end of the locking block, the whole locking block is accommodated in the clamping slot and forms a limiting clamp with the inner wall of the clamping slot.

Figure 6A:
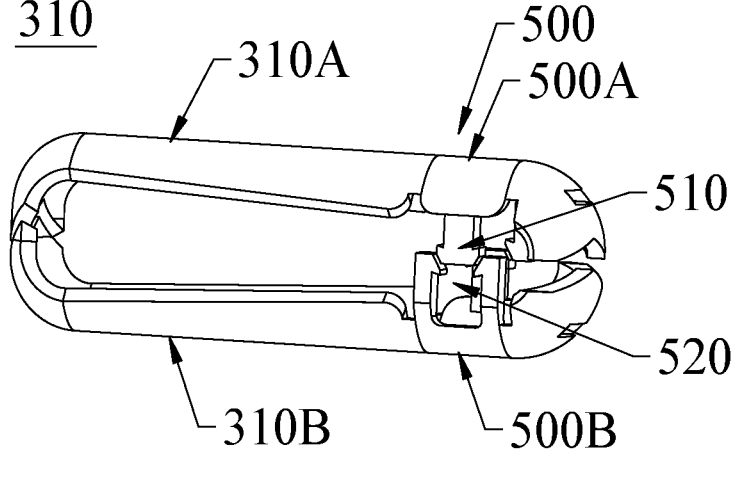
FIGS. 6A and 6B are schematic diagrams illustrating a matching process of a first locking part and a second locking part according to some other embodiments of the present disclosure.
Figure 6B:
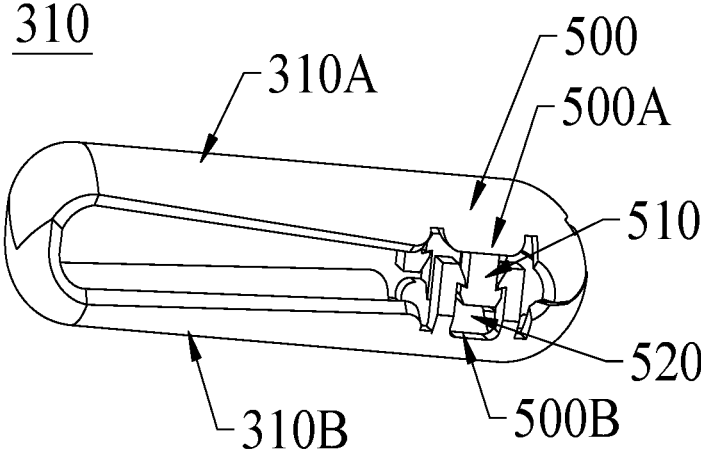

FIGS. 6A and 6B are schematic diagrams illustrating a matching process of a first locking part 500A and a second locking part 500B according to some other embodiments of the present disclosure.

As shown in FIGS. 6A and 6B, in some embodiments, the locking part 500 may be integrally formed with the at least two clips 310 to reduce components and simplify the structure of the clip arm 300. The first locking part 500A may be integrally formed with the first clip 310A. For example, the first locking part 500A may be formed at the proximal end of the first clip 310A. The second locking part 500B may be integrally formed with the second clip 310B. For example, the second locking part 500B may be formed at the proximal end of the second clip 310B.

In some embodiments, a structure of the locking protrusion 510 may include a limit buckle, and a structure of the locking recess 520 may include a clamping socket. When the limit buckle and the clamping socket clamp, the first locking part 500A and the second locking part 500B may be locked. In some embodiments, one end of the limit buckle may be fixed to the first clip 310A and/or the second clip 310B, and another end of the limit buckle may form a clamping end with an abruptly increased cross-section. The clamping socket may include a limit groove formed by combining two supporting arms, a limit groove formed by cutting the first clip 310A and/or the second clip 310B, etc. The clamping socket may include an entrance for receiving the limit buckle. A cross-section of the entrance may be abruptly decreased relative to other positions to form a limiting end. After the clamping end of the limit buckle extends into the limiting end of the clamping socket to form a clamping connection, the first locking part 500A and the second locking part 500B may be locked, and the first clip 310A and the second clip 310B may also be locked.

As shown in FIG. 6A, the first clip 310A and the second clip 310B are in a closed and unlocked state. The limit buckle of the locking protrusion 510 and the clamping socket of the locking recess 520 may be close to each other, but the limit buckle has not extended into the clamping socket. As shown in FIG. 6B, the first clip 310A and the second clip 310B are in the locked state, the clamping end of the limit buckle extends into the limiting end of the clamping socket, and a clamping cooperation is formed.

In some embodiments, at least a portion of the locking part 500 may be made of a biodegradable material. The biodegradable material may include polylactic acid, polyglycolic acid, a medical biodegradable material based on magnesium, iron, tungsten, or the like, or any combination thereof. Generally, a hemostatic clamp retained in a body performs hemostasis on a mucosal tissue. After a period for self-healing of the mucosal tissue, the clamped tissue and the hemostatic clamp detach to a digestive tract, eventually being expelled from the body. In special cases where the clamped tissue is a deep muscle tissue and the clamped tissue is difficult to detach on its own, if at least a portion of the locking part 500 is made of the biodegradable material, the locking part 500 may degrade after the period for clamping and hemostasis, the locking part 500 may unlock the at least two clips 310, and the at least two clips 310 may be separated from the clamped tissue.

In some embodiments, the first locking part 500A and/or the second locking part 500B of the locking part 500 may be made of the biodegradable material. When the first locking part 500A and/or the second locking part 500B degrade, the locking of the locking part 500 may be released, and the at least two clips 310 may be separated from the clamped tissue. In some embodiments, a partial structure of the locking part 500 connecting to the at least two clips 310 may be made of the biodegradable material. When the partial structure of the locking part 500 made of the biodegradable material degrades, the locking part 500 may detach from the at least two clips 310 and release the at least two clips 310. The at least two clips 310 may be separated from the clamped tissue.

In some embodiments, a locking process of the at least two clips 310 may be controlled by the at least two extending parts 400. Each of the at least two extending parts 400 may move along a direction from a distal end of the extending part 400 to a proximal end of the extending part 400, causing the at least two clips 310 (or the clip arm 300) to switch from the open state to the closed state, and then switch from the closed state to the locked state. In some embodiments, after the at least two clips 310 are locked, when each of the at least two extending parts 400 may continue to move along the direction from the distal end of the extending part 400 to the proximal end of the extending part 400, the at least two extending parts 400 may be released from the at least two clips 310, and the clip arm 300 may be released from the sheath tube 210. More descriptions regarding the at least two extending parts may be found in FIGS. 7 to 9 and relative descriptions thereof.

FIG. 7 is a schematic diagram illustrating an exemplary releasing structure of at least two clips 310 and a sheath tube 210 according to some embodiments of the present disclosure, wherein the sheath tube 210 is shown in an axial section view.

In some embodiments, a distal end of the sheath tube 210 may include a resisting part 230, and a proximal end of the clip 310 may be disposed with a resisted part 320. After the resisting part 230 and the resisted part 320 abut against each other, when each of the at least two extending parts 400 continues to move from along the direction from the distal end of the extending part 400 to the proximal end of the extending part 400, the resisting part 230 may limit movement of the resisted part 320 along the direction from the distal end of the extending part to the proximal end of the extending part, and the extending part 400 may be released from the clip 310.

In some embodiments, when the clip arm 300 moves along the direction from the distal end to the proximal end until the resisted part 320 of the clip 310 abuts against the resisting part 230 of the sheath tube 210, a resistance may be generated and feedbacked to the sliding handle 120 (as shown in FIG. 1). The sliding handle 120 may feedback the resistance to a user (e.g., an operator). Therefore, the user may obtain that the at least two clips 310 have been closed or locked, and may determine subsequent operations based on actual situation(s). When it is determined that the at least two clips 310 have effectively clamped for hemostasis, the core shaft 220 may be pulled along the direction from the distal end to the proximal end. The resisting part 230 may limit the movement of the resisted part 320 along the direction from the distal end to the proximal end, the at least two extending parts 400 may be released from the at least two clips 310, and the at least two clips 310 may be released from the sheath tube 210. When it is determined that the at least two clips 310 need to be reopened to clamp at least one tissue 20 again, the core shaft 220 may be pushed along a direction from the proximal end to the distal end, and at least a portion of the at least two extending parts 400 may extend out of the sheath tube 210, causing that the at least two clips 310 are in the open state. Through the above process, the clip instrument 10 has a repeatable opening and closing function before the release, thereby improving the operability of the surgical operation(s).

In some embodiments, when the core shaft 220 moves along the direction from the proximal end to the distal end, the resisting part 230 at the distal end of the sheath tube 210 may limit the at least two extending parts 400 to completely escape from the channel of the sheath tube 210. That is, the distal end of the core shaft 220 may be limited to extend out of the distal end of the channel of the sheath tube 210, thereby preventing excessive opening of the clip arm 300.

Figure 8:
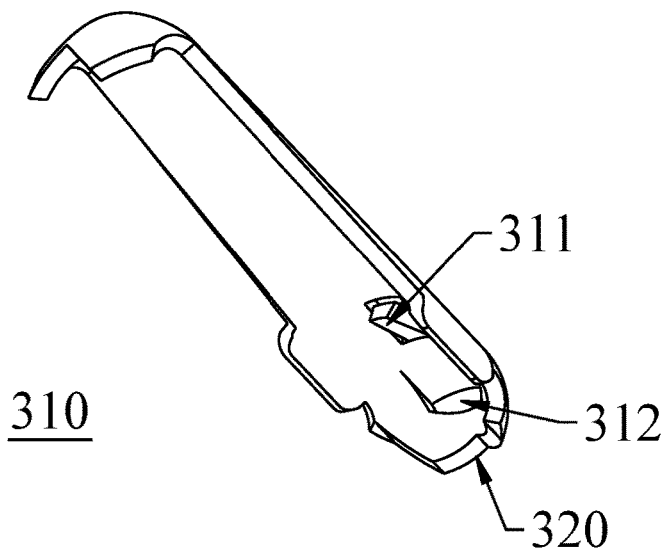
FIG. 8 is a diagram illustrating an exemplary structure of a clip according to some embodiments of the present disclosure.

FIG. 8 is a diagram illustrating an exemplary structure of a clip 310 according to some embodiments of the present disclosure.

As shown in FIGS. 7 and 8, in some embodiments, the proximal end of the clip 310 may be radially bent inward to form the resisted part 320, and the distal end of the sheath tube 210 may be disposed with a radially fixed limiting shaft. The limiting shaft may form the resisting part 230. When the clip 310 moves along the direction from the distal end to the proximal end, the resisted part 320 may abut against the limiting shaft. In some embodiments, a radial size of the resisted part 320 may be larger than an inner diameter of the distal end of the sheath tube 210, and an end surface of the distal end of the sheath tube 210 may form the resisting part 230. When the clip 310 moves along the direction from the distal end to the proximal end, the resisted part 320 may abut against the end surface of the distal end of the sheath tube 210, preventing the clip 310 from entering the sheath tube 210. In some embodiments, the distal end of the sheath tube 210 may form a radially inward protrusion to form the resisting part 230. The resisted part 320 of the clip 310 may abut against the protrusion to limit the movement of the clip 310 along the direction from the distal end to the proximal end.

As shown in FIG. 7, in some embodiments, the at least two extending parts 400 may include a first extending part 400A and a second extending part 400B. Proximal ends of both the first extending part 400A and the second extending part 400B may be connected to the core shaft 220, a distal end of the first extending part 400A may be releasably connected to the first clip 310A, and a distal end of the second extending part 400B may be releasably connected to the second clip 310B. The at least two extending parts 400 may control the opening and closing of the first clip 310A and the second clip 310B to clamp the at least one tissue 20, and improve an opening span between the first clip 310A and the second clip 310B. The at least two extending parts 400 may be released from the at least two clips 310, which can leave the at least two clips 310 with a relatively small size in the body, thereby reducing impact on the body.

Figure 9:
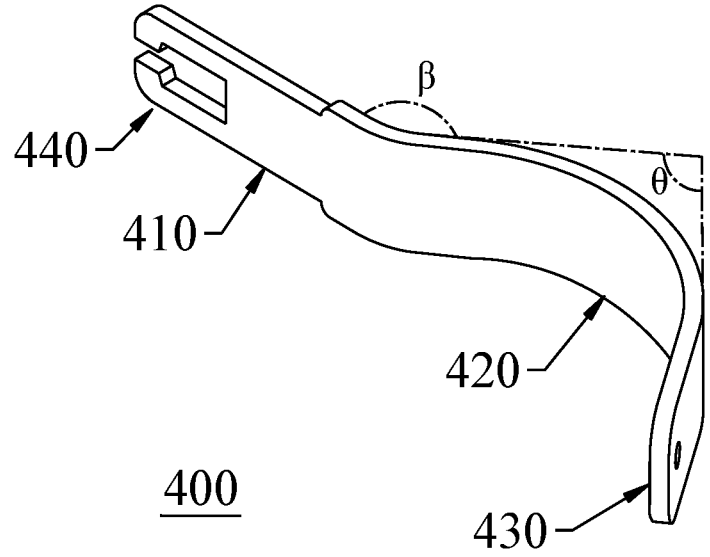
FIG. 9 is a schematic diagram illustrating an exemplary structure of an extending part according to some embodiments of the present disclosure.

FIG. 9 is a schematic diagram illustrating an exemplary structure of an extending part 400 according to some embodiments of the present disclosure.

As shown in FIGS. 7 and 9, in some embodiments, each of the first extending part 400A and the second extending part 400B may be disposed with a distal coupling part 410, a bending part 420, and a proximal coupling part 430. The distal coupling part 410 may be releasably connected to one of the at least two clips 310, the bending part 420 may be connected to the distal coupling part 410 and the proximal coupling part 430, and the proximal coupling part 430 may be connected to the core shaft 220.

In some embodiments, the bending part 420 may have elasticity. For example, the bending part 420 may be made of materials, such as stainless steel, etc. When the clip arm 300 is in the open state, the bending part 420 may cause the distal coupling part 410 of the first extending part 400A and the distal coupling part 410 of the second extending part 400B to move away from each other, thereby opening the first clip 310A and the second clip 310B. When the clip arm 300 is in the closed state, the bending part 420 may deform to provide a locking force for the locking part 500. In some embodiments, the bending part 420 may have elasticity. When the bending part 420 is located outside the channel of the sheath tube 210, the bending part 420 may be a curved shape, and the distal coupling part 410, the bending part 420, and the proximal coupling part 430 may not be collinear. When the bending part 420 enters the channel of the sheath tube 210, the bending part 420 may be compressed into a straight or approximately straight shape, and the distal coupling part 410, the bending part 420, and the proximal coupling part 430 may be collinear or substantially collinear. The "approximately straight shape" refers to that the bending part 420 has a linear structure that allows for a slight degree of bending. The bending part 420 may be contained within the channel of the sheath tube 210, which can save space. When the bending part 420 is located outside the channel of the sheath tube 210, a clipping span between the at least two clips 310 may be improved to clamp the at least one tissue 20.

In order to reduce structures left in the body and potential risks to the body, the clip instrument 10 in some embodiments of the present disclosure may not be disposed with a containment tube. After the at least two clips 310 are locked and separated from the at least two extending parts 400, only the at least two clips 310 may be remained in the body. Without the containment tube, the at least two clips 310 may not be subjected to a radially outward force from the at least two clips 310 during the locking process. Therefore, in some embodiments, by setting the shape of the bending part 420, the at least two extending parts 400 can provide the locking force to the at least two clips 310.

In some embodiments, the bending part 420 may include an arc-shaped structure. A bending angle $\theta$ of the bending part 420 refers to an included angle formed by sections at two end points of the bending part 420. The smaller the bending angle $\theta$, the larger an opening span and a clamping force of the first clip 310A and the second clip 310B. The larger the bending angle $\theta$, the smaller an operating force required for the first extending part 400A and the second extending part 400B during the clamping. In some embodiments, the bending angle $\theta$ may not be too large or too small. If the bending angle $\theta$ is too large, the opening span and the clamping force of the first clip 310A and the second clip 310B may be too small, that is difficult to clamp the tissue(s). If the bending angle $\theta$ is too small, the operating force required for the first extending part 400A and the second extending part 400B may be too large, that is difficult to operate and easy to cause fatigue of the bending part 420. In some embodiments, when the clip arm 300 is in the open state, the bending angle $\theta$ of the bending part 420 may be within a range from 30 degrees to 130 degrees. In some embodiments, when the clip arm 300 is in the open state, the bending angle $\theta$ of the bending part 420 may be within a range from 25 degrees to 125 degrees. For example, the bending angle $\theta$ may be 100 degrees. In some embodiments, when the clip arm 300 is in the open state, the bending angle θ of the bending part 420 may be within a range from 45 degrees to 100 degrees. In some embodiments, when the clip arm 300 is in the open state, the bending angle θ of the bending part 420 may be within a range from 60 degrees to 90 degrees. By setting the bending angle θ within the above ranges, the opening span between the first clip 310A and the second clip 310B can be improved, facilitating closing relatively large wound tissue(s). In addition, by setting the bending angle θ within the above ranges, a suitable clamping force for the tissue(s) can be provided, ensuring secure tissue clamping without excessive compression. Moreover, by setting the bending angle θ within the above ranges, the operating force required for the first extending part 400A and the second extending part 400B can be within an appropriate range, which can be the operation effortless and provide suitable feedback resistance to the user.

In some embodiments, the bending part 420 may bend outwardly along a radial direction, and the distal coupling part 410 may bend inwardly along the radial direction with respect to the bending part 420, so as to form an angle β. The angle β may be set within an appropriate range. If the angle β is too small, the first clip 310A and the second clip 310B may radially converge in the closed state, and the at least two extending parts 400 may not generate enough deformation to provide the locking force for the locking part 500. If the angle β is too large, the close of the clip 310 may be affected, which requires the user to exert a larger force to close the clamp. In addition, excessive deformation of the at least two extending parts 400 during the locking process may lead to the fatigue and fracture of the at least two extending parts 400. Therefore, in some embodiments, when the clip arm 300 is in the open state, the angle β between the distal coupling part 410 and a section at a connection between the distal coupling part 410 and the bending part 420 may be within a range from 95 degrees to 115 degrees. For example, the angle β may be 100 degrees. In some embodiments, when the clip arm 300 is in the open state, the angle β between the distal coupling part 410 and the section at the connection between the distal coupling part 410 and the bending part 420 may be within a range from 60 degrees to 150 degrees. In some embodiments, when the clip arm 300 is in the open state, the angle β between the distal coupling part 410 and the section at the connection between the distal coupling part 410 and the bending part 420 may be within a range from 90 degrees to 135 degrees. In some embodiments, when the clip arm 300 is in the open state, the angle β between the distal coupling part 410 and the section at the connection between the distal coupling part 410 and the bending part 420 may be within a range from 100 degrees to 110 degrees. By setting the angle β within the above ranges, the first clip 310A and the second clip 310B can radially converge when the clip arm 300 is in the closed state, and the at least two extending parts 400 can generate sufficient deformation and elastic force. The elastic force can provide the locking force for the locking part 500 to lock. Moreover, when the angle β is within the above ranges, the operating force of the user may be appropriate, which is labor-saving and convenient. In addition, by controlling the deformation of the at least two extending parts 400 during the locking, the at least two extending parts 400 can not be easy to fatigue, thereby increasing the service life of the at least two extending parts 400.

Figure 10:
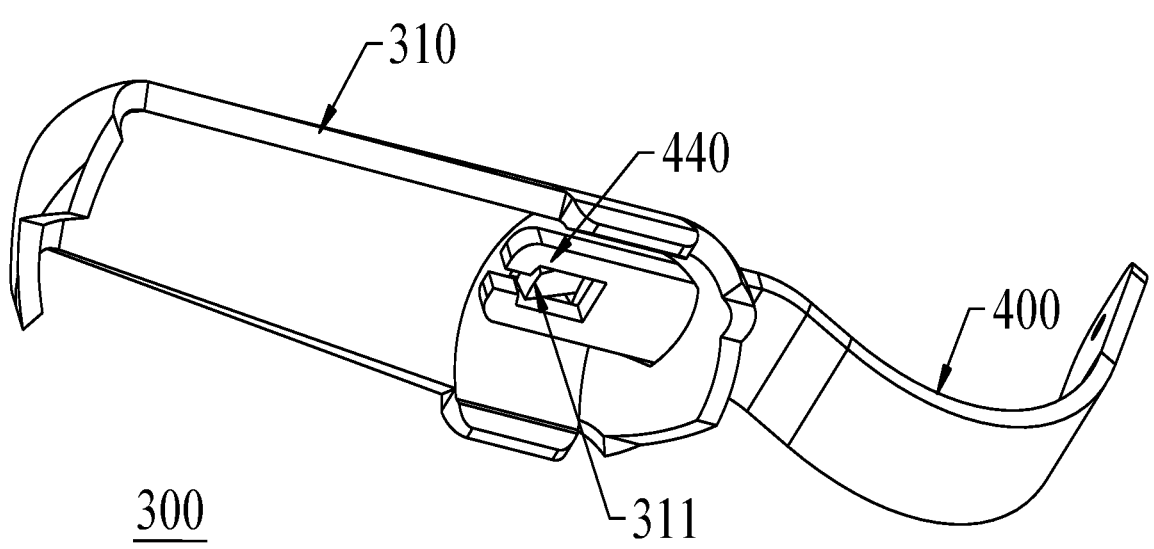
FIG. 10 is a schematic diagram illustrating an exemplary structure of coordination between a clip and an extending part according to some embodiments of the present disclosure.

FIG. 10 is a schematic diagram illustrating an exemplary structure of coordination between a clip 310 and an extending part 400 according to some embodiments of the present disclosure.

As shown in FIGS. 8 and 10, the clip 310 may be disposed with a first connecting part 311. In some embodiments, the first connecting part 311 may include a shrapnel protruding radially inward. Deformation, fracture, or displacement of the shrapnel may occur under a force. In some other embodiments, the first connecting part 311 may be a rigid structure, such as a rigid protruding tab.

As shown in FIGS. 9 and 10, the distal end of the extending part 400 may be disposed with a second connecting part 440. In some embodiments, the second connecting part 440 may include a limit buckle. Deformation, fracture, or displacement of the limit buckle may occur under a force. In some other embodiments, the second connecting part 440 may be a rigid structure.

As shown in FIG. 10, the first connecting part 311 and the second connecting part 440 may cooperate with each other to cause the clip 310 to be releasably connected to the extending part 400. In some embodiments, the limit buckle may be releasably clamped with the shrapnel. When the extending part 400 moves along the direction from the distal end of the extending part 400 to the proximal end of the extending part 400, the limit buckle may generate a force on the shrapnel along the direction from the distal end to the proximal end. When the force generated by the limit buckle on the shrapnel is less than a preset threshold, the limit buckle may remain cooperation with the shrapnel, and the clip 310 may remain cooperation with the extending part 400. When the force generated by the limit buckle on the shrapnel is larger than or equal to the preset threshold, the limit buckle may separate from the shrapnel, and the clip 310 may be released from the extending part 400.

In some embodiments, a proximal end of the first connecting part 311 may be connected to the clip 310, and a distal end of the first connecting part 311 may protrude inwardly from an inner sidewall of the clip 310. The second connecting part 440 may include two arms with bent hooks at distal ends of the two arms. The first connecting part 311 may be located between the two arms of the second connecting portion 440, and the distal end of the first connecting part 311 may abut against the bent hooks of the two arms. When the extending part 400 moves along the direction from the distal end of the extending part 400 to the proximal end of the extending part 400, the bent hooks of the two arms may drive the clip 310 to move from the distal end to the proximal end.

In some embodiments, as shown in FIGS. 8 and 10, a through-hole 312 may be formed at the proximal end of the clip 310. The distal coupling part 410 of the extending part 400 may pass through the through-hole 312 to cause the second connecting part 440 to cooperate with the first connecting part 311 of the clip 310. In some embodiments, a width of the distal coupling part 410 of the extending part 400 may be less than or equal to a transverse size of the through-hole 312, and the transverse size of the through-hole 312 may be less than a width of the bending part 420. The transverse size of the through-hole 312 refers to a size in a width direction of the clip 310. Thus, a step may be formed at the connection between the distal coupling part 410 and the bending part 420. After the distal coupling part 410 passes through the through-hole 312, the step may abut against a proximal end surface of the through-hole 312, preventing the bending part 420 from passing through the through-hole 312. When the extending part 400 moves along the direction from the proximal end to the distal end, the step may push the clip 310 to move along the direction from the proximal end to the distal end.

In some embodiments, when deformation, fracture, or displacement of the first connecting part 311 and/or the second connecting part 440 occur under a force, the at least two extending parts 310 may be released from the at least two clips 400, respectively.

In some embodiments, the extending part 400 may be made of an elastic material, such as stainless steel, etc. The clip 310 may be not limited to an elastic material and may be made of the same material as the extending part 400. The clip 310 may also be made of a material such as a polymer material. In some embodiments, the clip 310 and the extending part 400 may be made of the same material, and the clip arm 300 may be integrally formed. That is, a stress weak point may be set on the clip arm 300, the clip 310 may be located at a distal end of the stress weak point, and the extending part 400 may be located at a proximal end of the stress weak point. When a preset force exerts on the stress weak point of the clip arm 300, the clip arm 300 may be damaged, causing the clip 310 and the extending part 400 to separate from each other. In some embodiments, the clip 310 and the extending part 400 may be made of the same material or different materials, and the clip arm 300 may be separately formed. That is, the clip 310 and the extending part 400 may be assembled to form the clip arm 300 for clamping the at least one tissue 20. A releasable connection (i.e., the first connecting part 311 and the second connecting part 440) may be disposed between the clip 310 and the extending part 400. When a force is exerted on the releasable connection, deformation, fracture, or displacement of the releasable connection may occur, causing the clip 310 and the extending part 400 to separate from each other. The releasable connection may be disposed at the clip 310 or at the extending part 400. Alternatively, the releasable connection may be a separate component used to releasably connect the clip 310 and the extending part 400. In some embodiments, an elasticity of the extending part 400 may be larger than an elasticity of the clip 310, which can open or close of the at least two clip 310 (or the clip arm 300) through the deformation of the extending part 400.

Figure 11A:
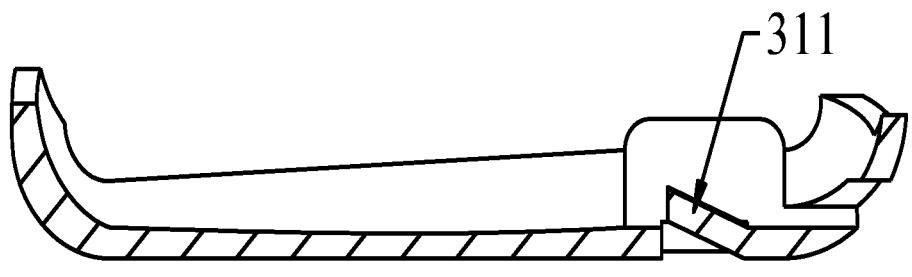
FIGS. 11A to 11C are schematic diagrams illustrating exemplary structures of clips when the clips release from extending parts according to some embodiments of the present disclosure.
Figure 11B:
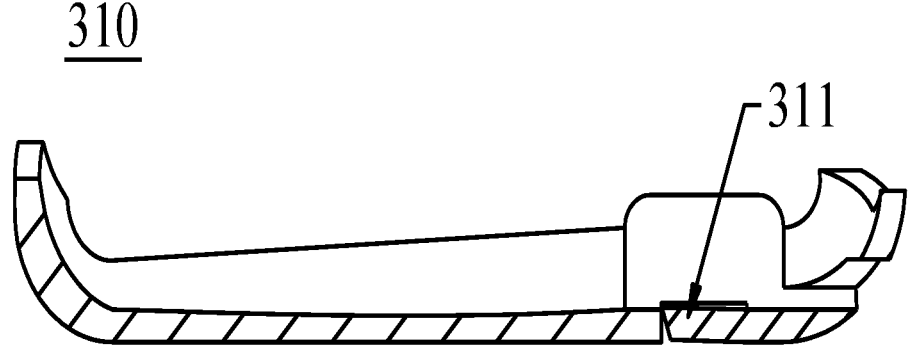
Figure 11C:
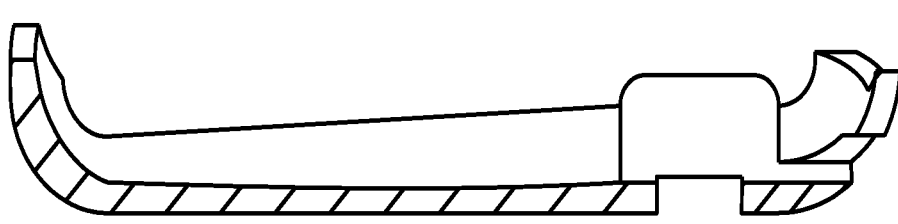

FIGS. 11A to 11C are schematic diagrams illustrating exemplary structures of clips when the clips release from extending parts according to some embodiments of the present disclosure.

As shown in FIG. 11A, in some embodiments, the first connecting part 311 may include an elastic structure. For example, the first connecting part 311 may include a shrapnel protruding radially inward, and the second connecting part 440 may include a limit buckle. In some embodiments, a stiffness of the second connecting part 440 may be larger than a stiffness of the first connecting part 311. For example, the stiffness of the second connecting part 440 may be not less than 2 times, 5 times, 10 times, etc., of the stiffness of the first connecting part 311. Alternatively, the second connecting part 440 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. The first connecting part 311 may deform under the force, which causes the distal end of the second connecting part 440 to pass over the first connecting part 311 and detach from first connecting part 311, thereby releasing the extending part 400 from the clip 310.

As shown in FIG. 11B, in some embodiments, the first connecting part 311 may include an elastic structure, such as a shrapnel. The second connecting part 440 may include a limit buckle. In some embodiments, the stiffness of the second connecting part 440 may be larger than the stiffness of the first connecting part 311. For example, the stiffness of the second connecting part 440 may be not less than 2 times, 5 times, 10 times, etc., of the stiffness of the first connecting part 311. Alternatively, the second connecting part 440 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. The first connecting part 311 may be displaced radially outward under the force, which causes the distal end of the second connecting part 440 to pass over the first connecting part 311 and detach from the first connecting part 311, thereby releasing the extending part 400 from the clip 310. In some embodiments, the first connecting part 311 may be rotatably disposed on the clip 310. The first connecting part 311 may be disposed to be flush with an inner surface of the clip 310 when the first connecting part 311 is not under a force, and protrude from the inner surface of the clip 310 when the first connecting part 311 is under the force. The inner surface of the clip 310 refers to a surface of the clip 310 close to a clamping space. Merely by way of example, the first connecting part 311 may be rotatably disposed on the clip 310 via a torsion spring or its material mechanical properties. When the first connecting part 311 cooperates with the second connecting part 440, the second connecting part 440 may apply a force to the first connecting part 311, causing the first connecting part 311 to protrude from the inner surface of the clip 310. As the extending part 400 moves the direction from the distal end to the proximal end, the distal end of the second connecting part 440 may pass over the first connecting part 311 and detach from the first connecting part 311, the force on the first connecting part 311 may be relieved, and the first connecting part 311 may return to be flush with the inner surface of the clip 310.

As shown in FIG. 11C, in some embodiments, the first connecting part 311 may include an elastic structure, such as a shrapnel. The second connecting part 440 may include a limit buckle. In some embodiments, the stiffness of the second connecting part 440 may be larger than the stiffness of the first connecting part 311. For example, the stiffness of the second connecting part 440 may be not less than 2 times, 5 times, 10 times, etc., of the stiffness of the first connecting part 311. Alternatively, the second connecting part 440 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. The first connecting part 311 may fracture under the force, which causes the second connecting part 440 to detach from the first connecting part 311, thereby releasing the extending part 400 from the clip 310.

Figure 12A:
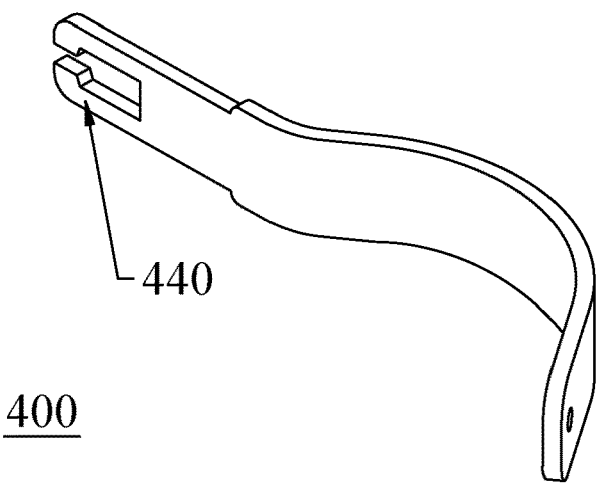
FIGS. 12A to 12C are schematic diagrams illustrating exemplary structures of extending parts when clips release from the extending parts according to some other embodiments of the present disclosure.
Figure 12B:
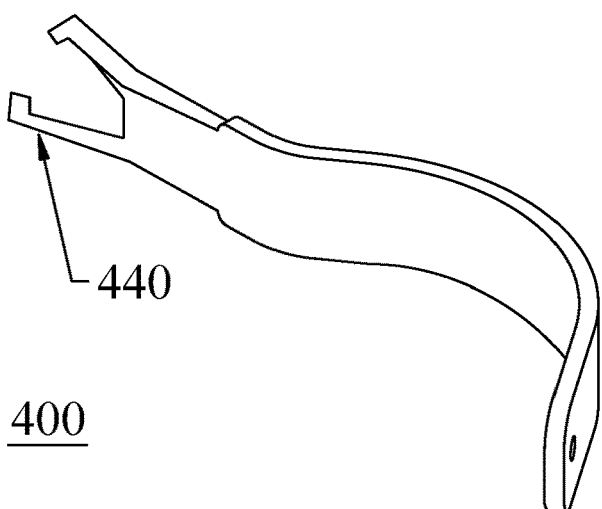
Figure 12C:
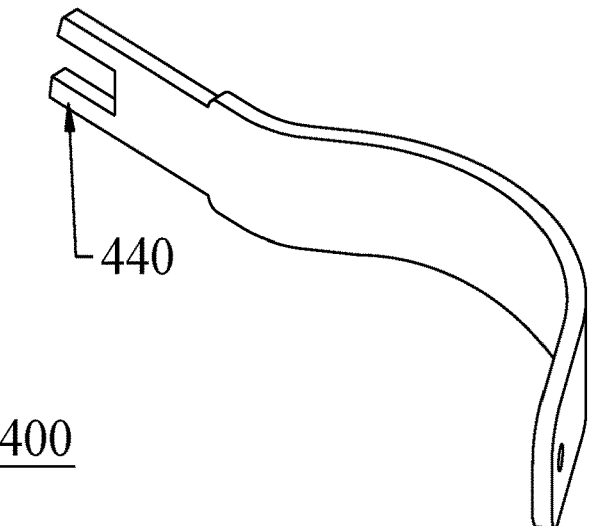

FIGS. 12A to 12C are schematic diagrams illustrating exemplary structures of extending parts when clips release from the extending parts according to some other embodiments of the present disclosure.

As shown in FIG. 12A, in some embodiments, the second connecting part 440 may include a semi-closed limit buckle including two hook-shaped arms. The first connecting part 311 may include an elastic structure, such as a shrapnel. In some embodiments, the stiffness of the second connecting part 440 may be larger than the stiffness of the first connecting part 311. For example, the stiffness of the second connecting part 440 may be not less than 2 times, 5 times, 10 times, etc., of the stiffness of the first connecting part 311. Alternatively, the second connecting part 440 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. Deformation, fracture, or displacement of the first connecting part 311 may occur under the force, and the second connecting part 440 may retain the original shape, which causes the second connecting part 440 to detach from the first connecting part 311, thereby releasing the extending part 400 from the clip 310.

As shown in FIG. 12B, in some embodiments, the second connecting part 440 may include an elastic structure, such as a semi-closed limit buckle including two hook-shaped arms. The first connecting part 311 may include a protruding tab. In some embodiments, the stiffness of the first connecting part 311 may be larger than the stiffness of the second connecting part 440. For example, the stiffness of the first connecting part 311 may be not less than 2 times, 5 times, 10 times, etc., of the stiffness of the second connecting part 440. Alternatively, the first connecting part 311 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. Deformation of the second connecting part 440 may occur under the force to open the two arms, and the first connecting part 311 may retain the original shape, which causes the second connecting part 440 to detach from the first connecting part 311, thereby releasing the extending part 400 from the clip 310.

As shown in FIG. 12C, in some embodiments, the second connecting part 440 may include an elastic structure, such as a semi-closed limit buckle including two hook-shaped arms. The first connecting part 311 may include a protruding tab. In some embodiments, the stiffness of the first connecting part 311 may be larger than the stiffness of the second connecting part 440. For example, the stiffness of the first connecting part 311 may be not less than 2 times, 5 times, 10 times, etc., of the stiffness of the second connecting part 440. Alternatively, the first connecting part 311 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. Fractures of hooks at the distal ends of the hook-shaped arms may occur under the force, and the first connecting part 311 may retain the original shape, which causes the second connecting part 440 to detach from the first connecting part 311, thereby releasing the extending part 400 from the clip 310.

Figure 13A:
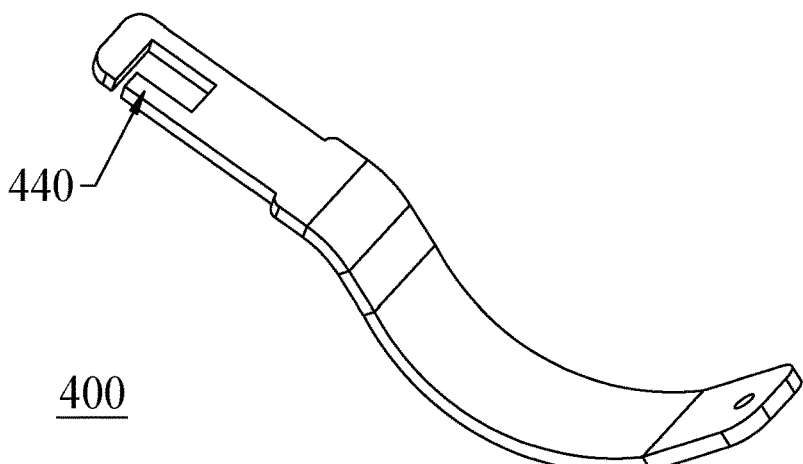
FIGS. 13A to 13C are schematic diagrams illustrating exemplary structures of extending parts when clips release from the extending parts according to some other embodiments of the present disclosure.
Figure 13B:
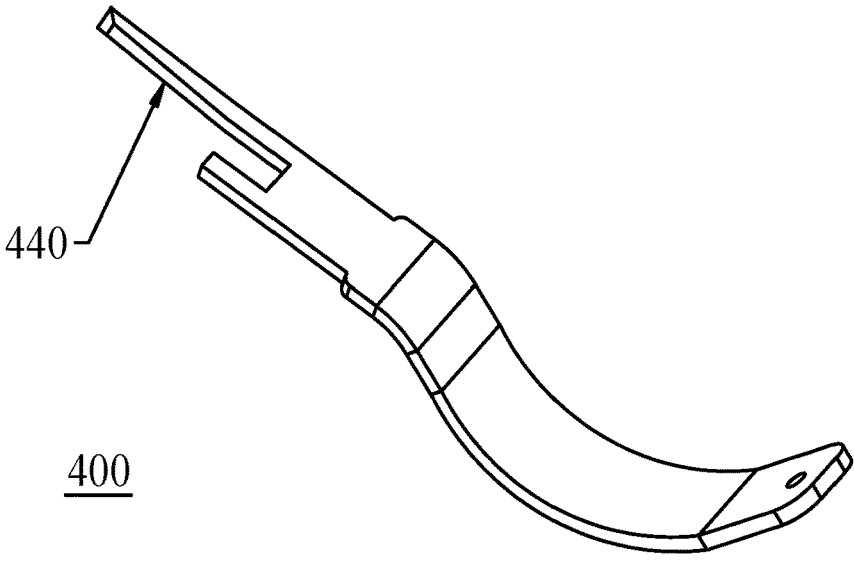
Figure 13C:
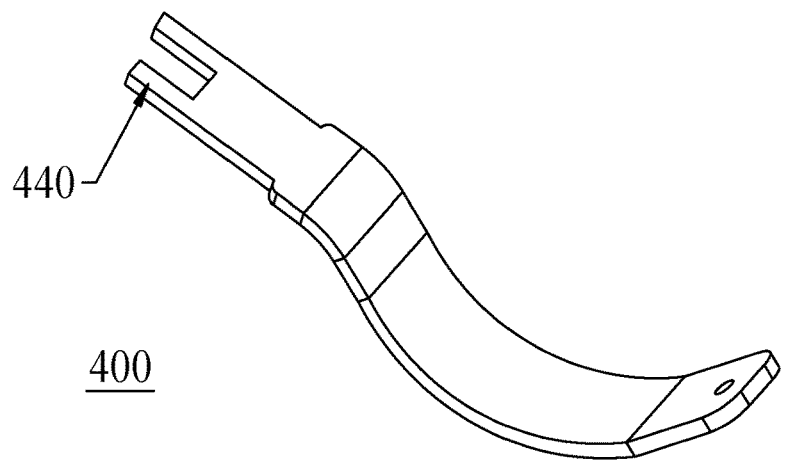

FIGS. 13A to 13C are schematic diagrams illustrating exemplary structures of extending parts when clips release from the extending parts according to some other embodiments of the present disclosure.

As shown in FIG. 13A, in some embodiments, the second connecting part 440 may include a semi-closed limit buckle including a gap. The first connecting part 311 may include an elastic structure, such as a shrapnel. In some embodiments, the stiffness of the second connecting part 440 may be larger than the stiffness of the first connecting part 311. For example, the stiffness of the second connecting part 440 may be not less than 2 times, 5 times, 10 times, etc., of the stiffness of the first connecting part 311. Alternatively, the second connecting part 440 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. Deformation, fracture, or displacement of the first connecting part 311 may occur under the force, and the second connecting part 440 may retain the original shape, which causes the second connecting part 440 to detach from the first connecting part 311, thereby releasing the extending part 400 from the clip 310.

As shown in FIG. 13B, in some embodiments, the second connecting part 440 may include an elastic structure, such as a semi-closed limit buckle including a gap and a stress weak point. The stress weak point may include a bending position of the limit buckle, a position of the limit buckle prone to deformation, or the like, or any combination thereof. In some embodiments, the stiffness of the first connecting part 311 may be larger than the stiffness of the second connecting part 440. For example, the stiffness of the first connecting part 311 may be not less than 2 times, 5 times, 10 times, etc., of the stiffness of the second connecting part 440. Alternatively, the first connecting part 311 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. Deformation of the second connecting part 440 may occur from the gap and the stress weak point of the second connecting part 440 under the force, and the first connecting part 311 may retain the original shape, which causes the second connecting part 440 to detach from the first connecting part 311, thereby releasing the extending part 400 from the clip 310.

As shown in FIG. 13C, in some embodiments, the second connecting part 440 may include an elastic structure, such as a semi-closed limit buckle including a gap and a stress weak point. The stress weak point may include a bending position of the limit buckle, a position of the limit buckle prone to fracture, or the like, or any combination thereof. In some embodiments, the stiffness of the first connecting part 311 may be larger than the stiffness of the second connecting part 440. For example, the stiffness of the first connecting part 311 may be not less than 2 times, 5 times, 10 times, etc., of the stiffness of the second connecting part 440. Alternatively, the first connecting part 311 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. Fracture of the second connecting part 440 may occur from the gap and the stress weak point of the second connecting part 440 under the force, and the first connecting part 311 may retain the original shape, which causes the second connecting part 440 to detach from the first connecting part 311, thereby releasing the extending part 400 from the clip 310.

Figure 14A:
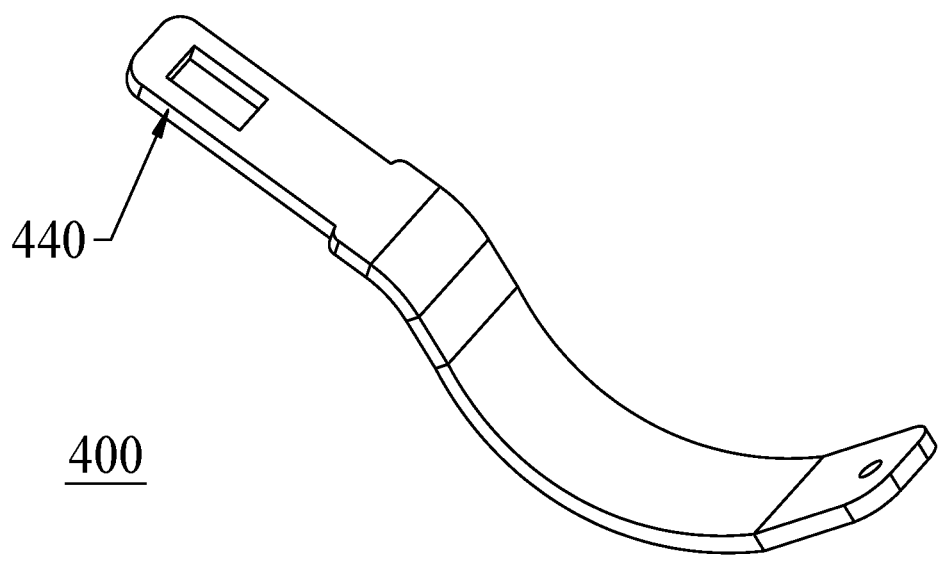
FIGS. 14A and 14B are schematic diagrams illustrating exemplary structures of extending parts when clips release from the extending parts according to some other embodiments of the present disclosure.
Figure 14B:
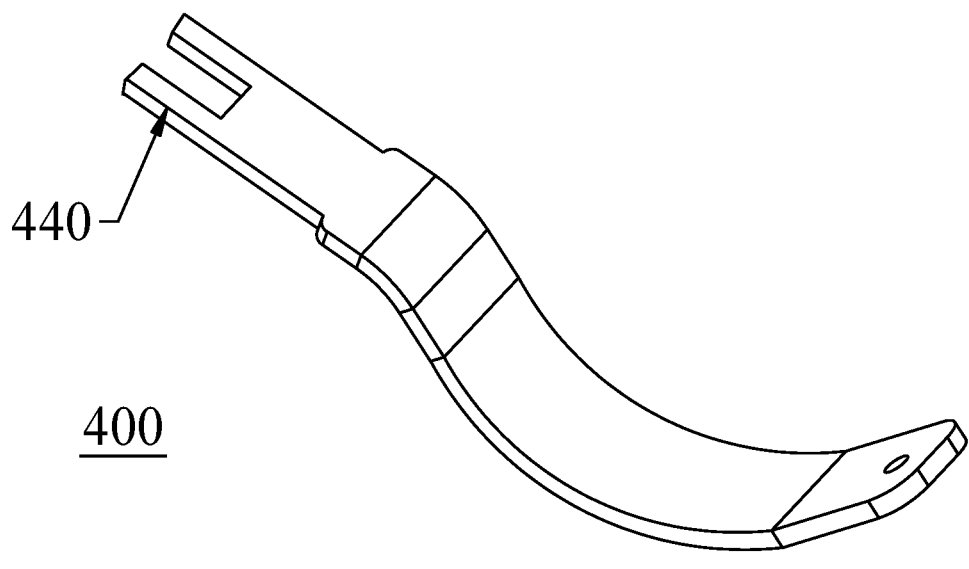

FIGS. 14A and 14B are schematic diagrams illustrating exemplary structures of extending parts when clips release from the extending parts according to some other embodiments of the present disclosure.

As shown in FIG. 14A, in some embodiments, the second connecting part 440 may include a closed limit buckle. The first connecting part 311 may include an elastic structure, such as a shrapnel. In some embodiments, the stiffness of the second connecting part 440 may be larger than the stiffness of the first connecting part 311. For example, the stiffness of the second connecting part 440 may be not less than 2 times, 5 times, 10 times, etc., of the stiffness of the first connecting part 311. Alternatively, the second connecting part 440 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. Deformation, fracture, or displacement of the first connecting part 311 may occur under the force, and the second connecting part 440 may retain the original shape, which causes the second connecting part 440 to detach from the first connecting part 311, thereby releasing the extending part 400 from the clip 310.

As shown in FIG. 14B, in some embodiments, the second connecting part 440 may include an elastic structure, such as a closed limit buckle including a stress weak point. The stress weak point may include a bending position of the limit buckle, a position of the limit buckle prone to fracture, or the like, or any combination thereof. In some embodiments, the stiffness of the first connecting part 311 may be larger than the stiffness of the second connecting part 440. For example, the stiffness of the first connecting part 311 may be not less than 2 times, 5 times, 10 times, etc., of the stiffness of the second connecting part 440. Alternatively, the first connecting part 311 may be a rigid structure. When the extending part 400 moves along the direction from the distal end of the extending part 400 to the proximal end of the extending part 400, the second connecting part 440 may exert a force on the first connecting part 311 along the direction from the distal end to the proximal end. Fracture of the second connecting part 440 may occur from the stress weak point of the second connecting part 440 under the force, and the first connecting part 311 may retain the original shape, which causes the second connecting part 440 to detach from the first connecting part 311, thereby releasing the extending part 400 from the clip 310.

FIGS. 15 to 18B are schematic diagrams illustrating a clamping process between clips 310 and extending parts 440 according to some embodiments of the present disclosure.

Figure 15:
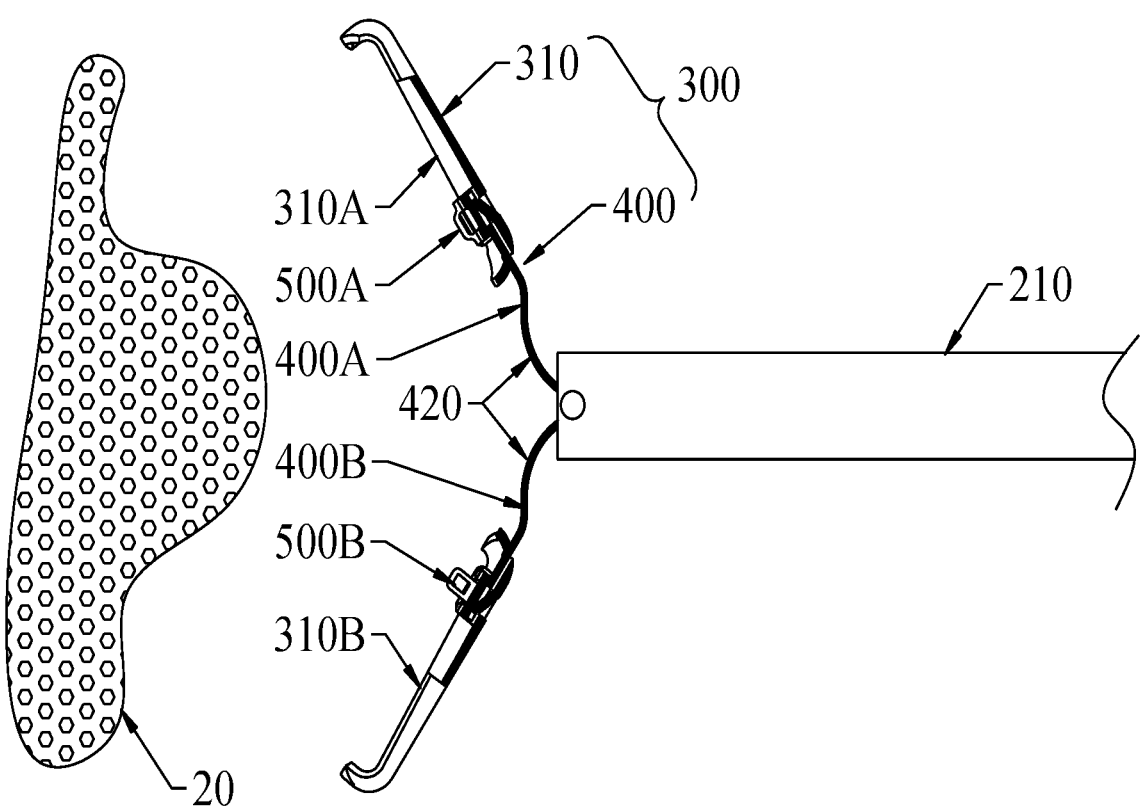
FIGS. 15 to 18B are schematic diagrams illustrating a clamping process between clips and extending parts according to some embodiments of the present disclosure.

In some embodiments, as shown in FIG. 15, the clip arm 300 may be in the open state. The at least two clips 310 and the at least two extending parts 400 may be connected, respectively. The core shaft 220 may move axially along the channel of the sheath tube 210 from the proximal end to the distal end, driving the clip arm 300 connected to the core shaft 220 to move along the direction from the proximal end to the distal end. The first extending part 400A and the second extending part 400B may move along the direction from the proximal end to the distal end to an outer side of the channel of the sheath tube 210. The first extending part 400A and the second extending part 400B may open and move away from each other under an elastic action of the bending part 420. The first clip arm 300A and the second clip 300B may move away from each other and form a clamping space for receiving the at least one tissue 20. The clip arm 300 may be in the open state, and the first locking part 500A disposed on the first clip 310A and the second locking part 500B disposed on the second clip 310B may move away from each other.

Figure 16A:
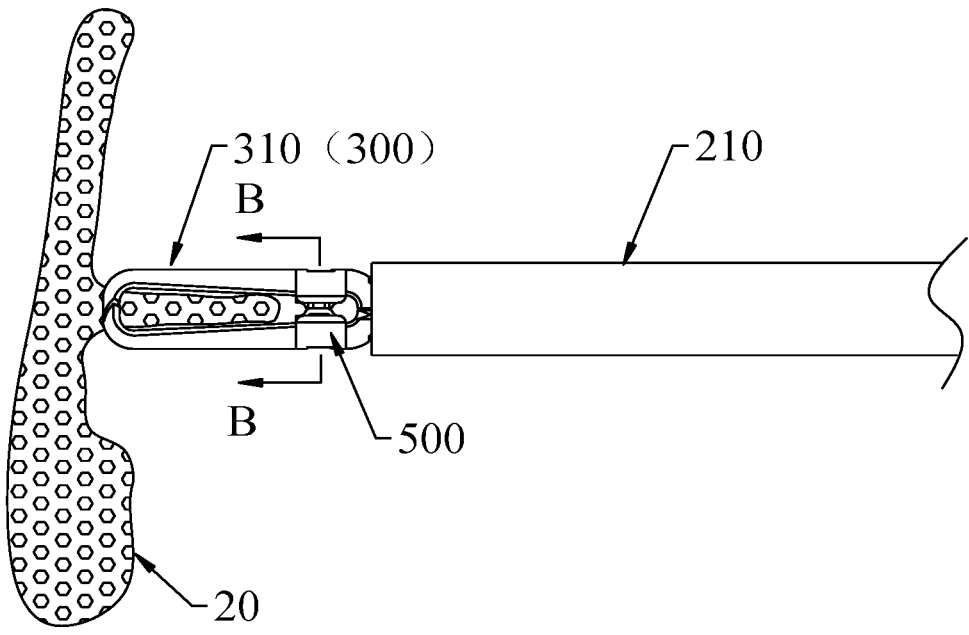
Figure 16B:
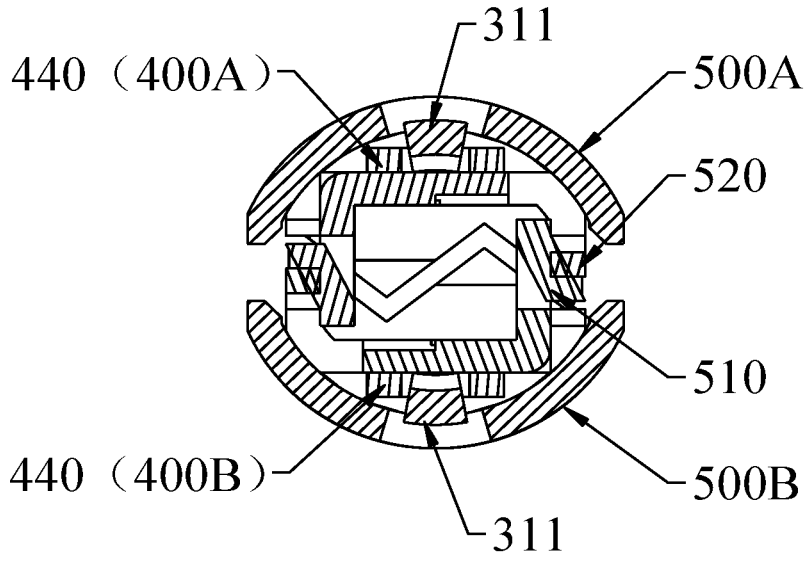

FIG. 16B is a schematic diagram illustrating an exemplary section of a clip instrument at a position B-B in FIG. 16A. In some embodiments, as shown in FIGS. 16A and 16B, the clip arm 300 (e.g., the first clip 310A and the second clip 3110B) may be close to each other and in an unlocked state. The at least two clips 310 and the at least two extending parts 400 may be connected, respectively. The core shaft 220 may move axially along the channel of the sheath tube 210 from the proximal end to the distal end, driving the clip arm 300 connected to the core shaft 220 to move along the direction from the proximal end to the distal end. The first extending part 400A and the second extending part 400B may be accommodated inside the channel of the sheath tube 210. When the resisted part 320 at the proximal end of each of the at least two clips 310 moves to the resisting part 230 at the distal end of the sheath tube 210, a resistance force may be generated through mutual abutment between the resisted part 320 and the resisting part 230, which can provide feedback to the user. The user may continue to push the core shaft 220 along the direction from the proximal end to the distal end or pull the core shaft 220 along the direction from the distal end to the proximal end based on the feedback. If the core shaft 220 is pushed along the direction from the proximal end to the distal end, the clip arm 300 may be switched from the closed state to the open state. More descriptions regarding the switch of the clip arm 300 may be found in FIG. 15 and relative descriptions thereof. If the core shaft 220 is pulled along the direction from the distal end to the proximal end, the clip arm 300 may continue to close and generate the locking force for the locking part 500. In some embodiments, the control part 100 may include an automatic control handle. After the clip arm 300 is closed, the automatic control handle may automatically apply a tension to the core shaft 220 for a preset duration based on actual requirement(s), causing the clip arm 300 to generate the locking force on the locking part 500 for the preset duration. In some embodiments, whether the at least two clips 310 are locked by the locking part 500 may be determined, and the tension may be adjusted based on the determination result. For example, if it is determined that the locking part 500 has not locked the at least two clips 310, the automatic control handle may increase the tension on the core shaft 220. By automatically applying the tension on the core shaft 220 for the preset duration, a surgical operation can be simplified. In addition, the operation difficulty of the user can be reduced through the combination of automatic and manual operations. In some embodiments, as shown in FIG. 16B, the two clips 310 of the clip arm 300 may be close to each other but not completely closed. The locking protrusion 510 and/or the locking recess 520 of the first locking part 500A and the locking recess 520 and/or the locking protrusion 510 of the second locking part 500B may be close to each other but have not cooperated with each other.

Figure 17A:
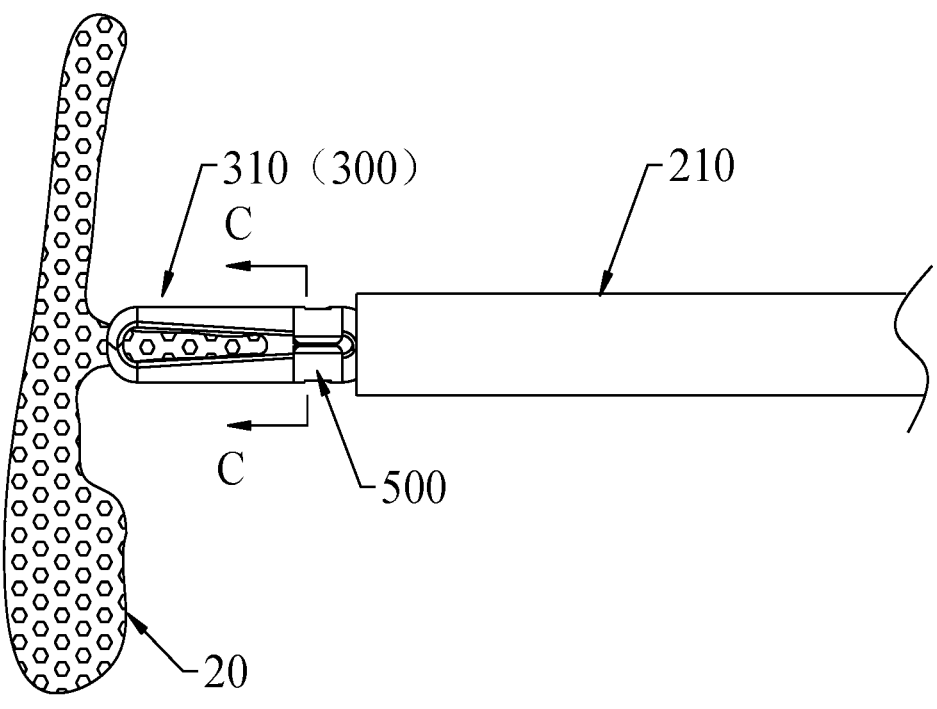
Figure 17B:
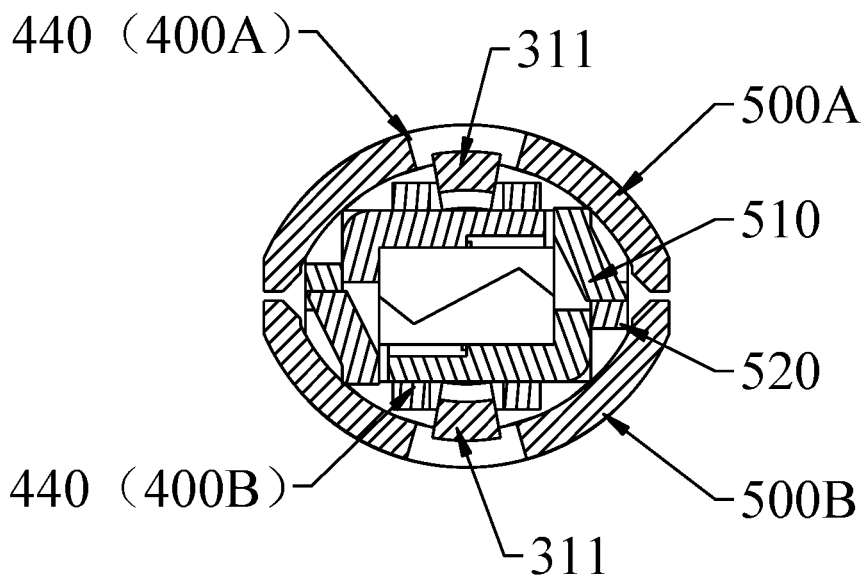

FIG. 17B is a schematic diagram illustrating an exemplary section of a clip instrument at a position C-C in FIG. 17A. In some embodiments, as shown in FIGS. 17A and 17B, the clip arm 300 (e.g., the at least two clips 310) may be in a closed and locked state. The at least two clips 310 and the at least two extending parts 400 may be connected.

In some embodiments, after the clip arm 300 (e.g., the at least two clips 310) are close to each other (as shown in FIG. 16B), the core shaft 220 may continue to move along the channel of the sheath tube 210 from the distal end to the proximal end. The first extending part 400A and the second extending part 400B may continue to enter the sheath tube 210 and be compressed, causing the distal coupling parts 410 to continue to approach each other. The first extending part 400A and the second extending part 400B may apply a radial compression force on the at least two clips 310 under an elastic force of the bending part 420, causing the first clip 310A and the second clip 310B to continue to approach each other.

In some embodiments, after the clip arm 300 (e.g., the at least two clips 310) are close to each other (as shown in FIG. 16B), the core shaft 220 may continue to move along the channel of the sheath tube 210 from the distal end to the proximal end. The first extending part 400A and the second extending part 400B may continue to enter the sheath tube 210, driving the proximal ends of the at least two clips 310 to enter the distal end of the sheath tube 210. The sheath tube 210 may apply a radial compression force on the at least two clips 310, causing the first clip 310A and the second clip 310B to continue to approach each other.

The first clip 310A and the second clip 310B may continue to move radially inward under the elastic force applied by the bending part 420 and/or the compressive force applied by the sheath tube 210, thereby driving the locking protrusion 510 and/or the locking recess 520 of the first locking part 500A and the locking protrusion 510 and/or the locking recess 520 of the second locking part 500B to continue moving radially inward. The locking protrusion 510 may enter into the locking recess 520 for cooperation, causing the locking of the first clip 310A and the second clip 310B.

Figure 18A:
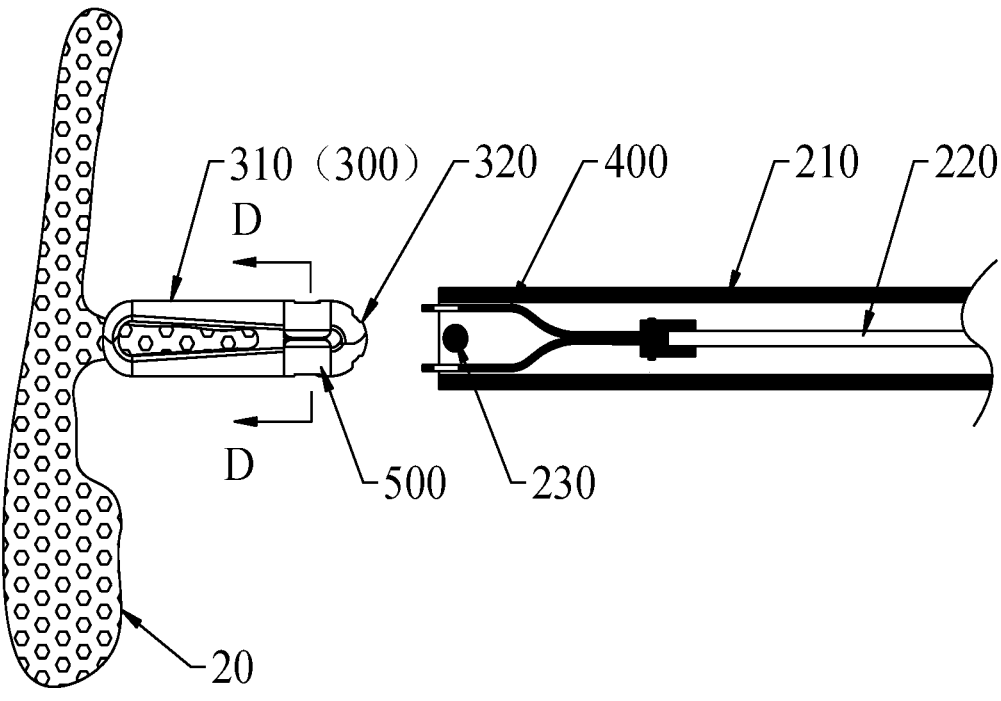
Figure 18B:
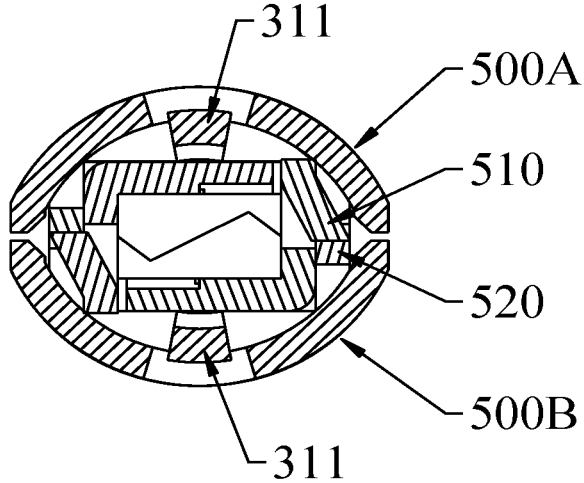

FIG. 18B is a schematic diagram illustrating an exemplary section of a clip instrument at a position D-D in FIG. 18A. In some embodiments, as shown in FIGS. 18A and 18B, the clip arm 300 (e.g., the at least two clips 310) may be in a released state. After the clip arm 300 is locked, the core shaft 220 may continue to move along the channel of the sheath tube 210 from the distal end to the proximal end. At this time, the resisted parts 320 of the at least two clips 310 and the resisting parts 230 at the distal end of the sheath tube 210 may be abutted. The at least two extending parts 400 may continue to move along the direction from the distal end to the proximal end, but the at least two clips 310 can not move from the distal end to the proximal end. As the at least two extending parts 400 continue to move along the direction from the distal end to the proximal end, the second connecting part 440 of the extending part 400 may separate from the first connecting part 311 of the clip 310 due to the deformation, displacement, or fracture. The at least two extending parts 400 may be released from the at least two clips 310, and the core shaft 220 may drive the at least two extending parts 400 to withdraw from the channel of the sheath tube 210. The at least two extending parts 400, the sheath tube 210, and the conveying part 200 for delivering the sheath tube 210 may be withdrawn from the body, leaving only the at least two clips 310 and the locking part 500 in the body, thereby reducing structures left in the body and minimizing potential risks to the body.

Embodiment Two of the present disclosure is described in detail below in combination with FIGS. 19 to 31. In the following descriptions, different parts between the clip instrument 10 in Embodiment Two and the clip instrument 10 in Embodiment One may be described. The same parts may be referred to the descriptions in Embodiment One, which is not repeated. Compared to Embodiment One, structures of the releasable connection between the at least two extending parts 400 and the at least two clips 310 and structures related to the locking part 500 in Embodiment Two may be different from those in Embodiment One.

Figure 19:
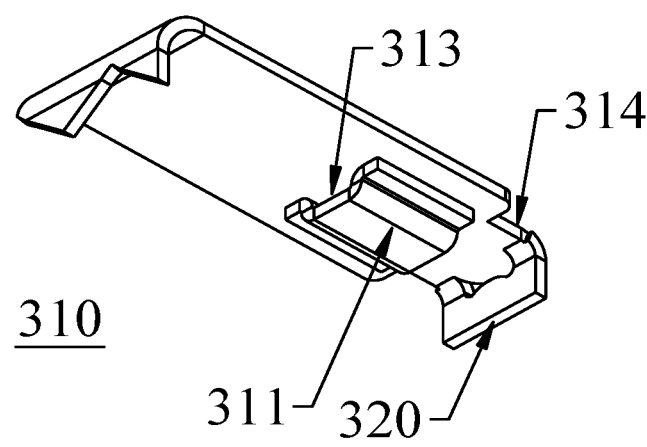
FIG. 19 is a schematic diagram illustrating an exemplary structure of a clip according to some embodiments of the present disclosure.
Figure 20:
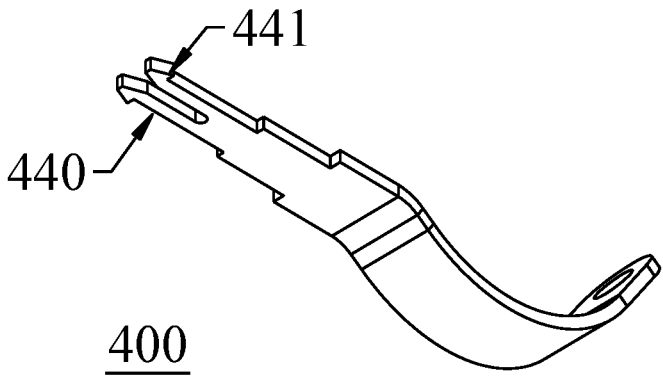
FIG. 20 is a schematic diagram illustrating an exemplary structure of an extending part according to some embodiments of the present disclosure.
Figure 21:
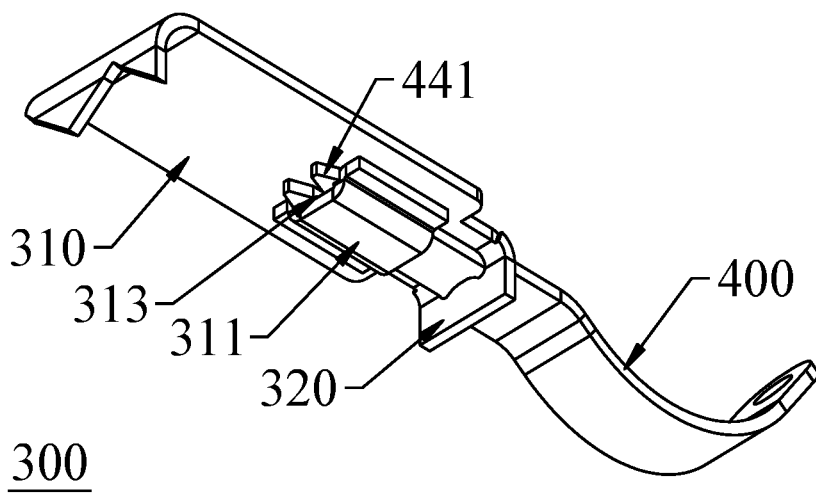
FIG. 21 is a schematic diagram illustrating an exemplary structure of coordination between a clip and an extending part according to some embodiments of the present disclosure.

FIG. 19 is a schematic diagram illustrating an exemplary structure of a clip 310 according to some embodiments of the present disclosure. FIG. 20 is a schematic diagram illustrating an exemplary structure of an extending part 400 according to some embodiments of the present disclosure. FIG. 21 is a schematic diagram illustrating an exemplary structure of coordination between a clip 310 and an extending part 400 according to some embodiments of the present disclosure.

In some embodiments, as shown in FIG. 19, the clip 310 may be disposed with a first connecting part 311. In some embodiments, the first connecting part 311 may include a limiting channel 313. The limiting channel 313 may be disposed along an axial direction of the clip 310.

In some embodiments, as shown in FIG. 20, a distal end of the extending part 400 may be disposed with a second connecting part 440. In some embodiments, a distal end of the second connecting part 440 may be disposed with at least one limiting protrusion 441. The at least one limiting protrusion 441 may deform, fracture, or displace under a force.

In some embodiments, as shown in FIG. 21, the second connecting part 440 may be inserted into the limiting channel 313. The limiting protrusion 441 may extend from a distal end of the limiting channel 313 and be releasably clamped with the limiting channel 313. When the limiting protrusion 441 is clamped at the distal end of the limiting channel 313, the extending part 400 may be connected to the clip 310. As the extending part 400 moves along a direction from the distal end of the extending part 400 to a proximal end of the extending part 400, the limiting protrusion 441 may deform, fracture, or displace, and detach from the distal end of the limiting channel 313, the distal end of the extending part 400 may be removed from the limiting channel 313, and the extending part 400 may be separated from the clip 310.

In some embodiments, the first connecting part 311 may be a rigid structure. The second connecting part 440 may include two arms. A radially outward limiting protrusion 441 may be disposed at a distal end of each of the two arms.

Figure 22A:
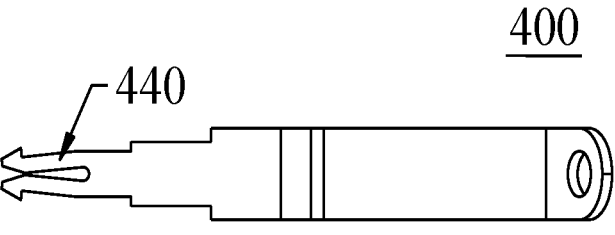
FIGS. 22A to 22C are schematic diagrams illustrating exemplary structures of extending parts after released from clips according to some other embodiments of the present disclosure.
Figure 22B:
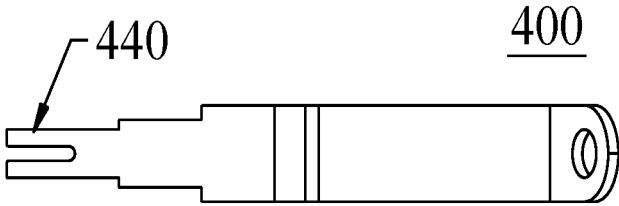
Figure 22C:
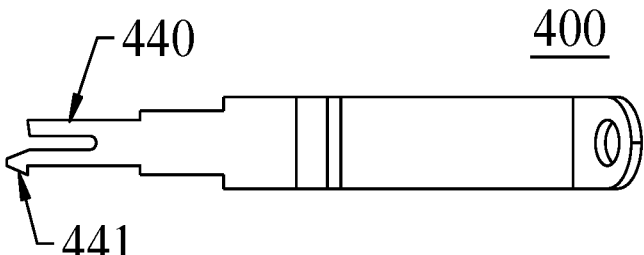

FIGS. 22A to 22C are schematic diagrams illustrating exemplary structures of extending parts after released from clips according to some other embodiments of the present disclosure.

As shown in FIG. 22A, in some embodiments, two arms of the second connecting part 440 may include elastic structures. As the extending part 400 moves along the direction from the distal end to the proximal end, the second connecting part 440 may apply a force on the first connecting part 311 along the direction from the distal end to the proximal end. The two arms of the second connecting part 440 may deform, causing the second connecting part 440 to contract radially inward. The first connecting part 311 may retain the original shape. The second connecting part 440 may detach from the first connecting part 311, and the extending part 400 may be released from the clip 310.

As shown in FIG. 22B, in some embodiments, stress weak points may be disposed at connections between the at least one limiting protrusion 441 of the second connecting part 440 and the two arms. As the extending part 400 moves along the direction from the distal end to the proximal end, the second connecting part 440 may apply a force on the first connecting part 311 along the direction from the distal end to the proximal end. The stress weak points of the second connecting part 440 may fracture under the force, causing the second connecting part 440 to detach from the first connecting part 311, thereby releasing the extending part 400 from the clip 310.

As shown in FIG. 22C, in some embodiments, one of the two arms of the second connecting part 440 may include an elastic structure, and a stress weak point may be disposed at a connection between the at least one limiting protrusion 441 and the other arm. As the extending part 400 moves along the direction from the distal end to the proximal end, the second connecting part 440 may apply a force on the first connecting part 311 along the direction from the distal end to the proximal end. One of the two arms of the second connecting part 440 may contract radially inward, while the other arm and the limiting protrusion 441 fracture at the stress weak point, causing the second connecting part 440 to detach from the first connecting part 311, thereby releasing the extending part 400 from the clip 310.

Figure 23:
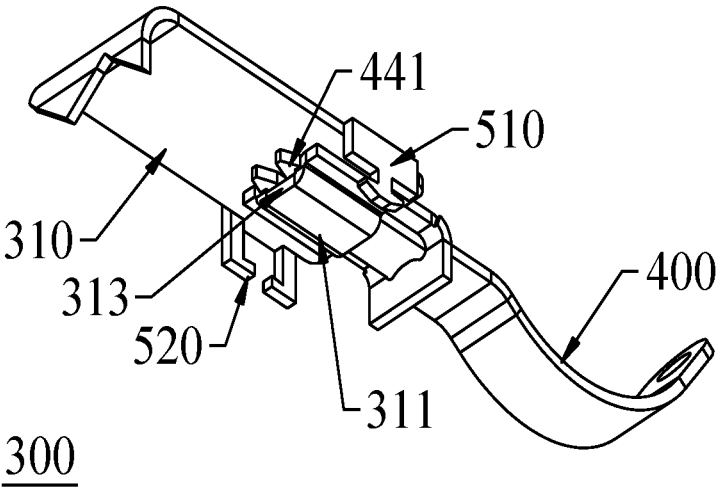
FIG. 23 is a schematic diagram illustrating an exemplary structure of coordination between a clip and an extending part according to some other embodiments of the present disclosure.

FIG. 23 is a schematic diagram illustrating an exemplary structure of coordination between a clip 310 and an extending part 400 according to some other embodiments of the present disclosure.

In some embodiments, the clip arm 300 may further include a locking part 500. The locking part 500 may be disposed on the at least two clips 310. The locking part 500 may be configured to maintain two of the at least two clips 310 (e.g., the first clip 310A and the second clip 310B) in the closed state. As shown in FIG. 23, a locking protrusion 510 and a locking recess 520 may be disposed on two sides of each of the two clips 310. The locking protrusion 510 and the locking recess 520 may cooperate with each other to lock the first clip 310A and the second clip 310B.

In some other embodiments, the clip arm 300 may further include a locking part 500 in other structural forms. For example, the locking part 500 may not be disposed on the at least two clips 310, but may be disposed on the sheath tube 210 or other locations. By adjusting a position of the locking part 500 with respect to the at least two clips 310, the locking part 500 may lock the at least two clips 310. In some embodiments, the locking part 500 may be disposed at the distal end of the sheath tube 210. After the at least two clips 310 move to the distal end of the sheath tube 210, the at least two clips 310 may form a locking cooperation with the locking part 500. In some embodiments, the locking part 500 may be disposed at an inner side of the channel of the sheath tube 210. A locked part 314 of each of the at least two clips 310 may move to the inner side of the channel of the sheath tube 210, and form a locking cooperation with the locking part 500. More descriptions regarding the locking cooperation may be found in FIGS. 24 to 26 and relative descriptions thereof.

Figure 24:
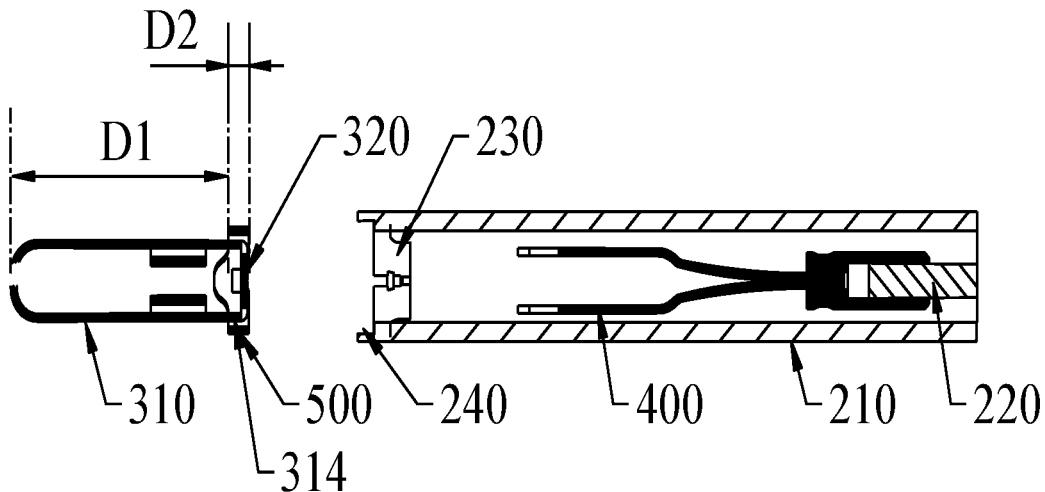
FIG. 24 is a sectional view of at least two clips and a sheath tube according to some embodiments of the present disclosure.
Figure 25A:
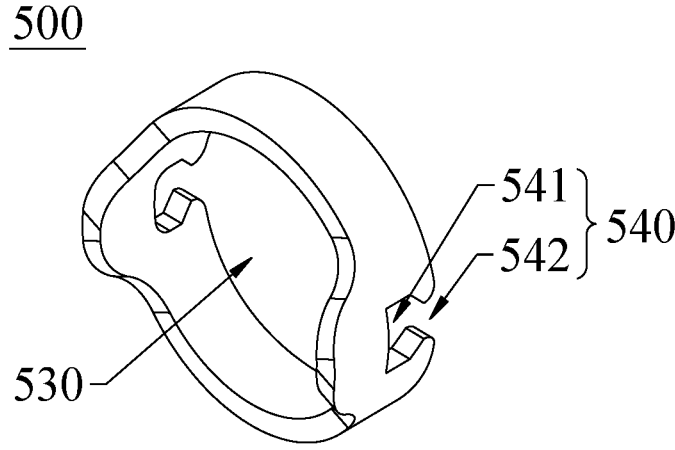
FIG. 25A is a schematic diagram illustrating an exemplary structure of a locking part according to some embodiments of the present disclosure.

FIG. 24 is a sectional view of at least two clips 310 and a sheath tube 210 according to some embodiments of the present disclosure. FIG. 25A is a schematic diagram illustrating an exemplary structure of a locking part 500 according to some embodiments of the present disclosure.

As shown in FIGS. 19, 24, and 25A, in some embodiments, a structure of the locking part 500 may include a tubular structure or an annular structure including a locking channel 530. In some embodiments, each of the at least two clips 310 may be disposed with a narrow part to form a locked part 314. The locked part 314 may cooperate (e.g., interference fit) with the locking part 500 to form a constraint. As the at least two clips 310 move along the direction from the distal end to the proximal end, the locked parted 314 may be clamped within a channel (e.g., the locking channel 530) of the locking part 500. In some embodiments, the locking part 500 may be releasably disposed at the distal end of the sheath tube 210. When the core shaft 220 drives the at least two clips 310 to move along the direction from the distal end to the proximal end through the at least two extending parts 400, the at least two clips 310 may be closed. The proximal ends of the at least two clips 310 may enter the locking part 500, causing the locking part 500 to clamp with the locked parted 314. The locking part 500 may limit radial displacements and axial displacements of the at least two clips 310, thereby maintaining the at least two clips 310 in the locked state.

As shown in FIG. 24, in some embodiments, the distal end of the sheath tube 210 may be disposed with a groove 240. The locking part 500 may be releasably accommodated in the groove 240. When the locking part 500 does not cooperate with the at least two clips 310, the locking part 500 may be disposed in the groove 240 of the sheath tube 210. After the locking part 500 cooperates with the at least two clips 310, the locking part 500 may separate from the groove 240 of the sheath tube 210, thereby releasing the at least two clips 310 from the sheath tube 210.

In some embodiments, after the at least two clips 310 are released from the sheath tube 210, the proximal ends of the at least two clips 310 may be accommodated in the locking channel 530 of the locking part 500, and the distal ends of the at least two clips 310 may be located outside the locking channel 530. A first axial length D1 of the distal end of each of the at least two clips 310 located outside the locking channel 530 may be larger than a second axial length D2 of the locking channel 530. For example, the first axial length D1 of the distal end of each of the at least two clips 310 located outside the locking channel 530 may be within a range from 4 millimeters to 10 millimeters, and the second axial length D2 of the locking channel 530 may be within a range from 0.5 millimeters to 3 millimeters. As another example, the first axial length D1 of the distal end of each of the at least two clips 310 located outside the locking channel 530 may be within a range from 2 millimeters to 13 millimeters, and the second axial length D2 of the locking channel 530 may be within a range from 0.2 millimeters to 5 millimeters. As yet another example, the first axial length D1 of the distal end of each of the at least two clips 310 located outside the locking channel 530 may be within a range from 5 millimeters to 8 millimeters, and the second axial length D2 of the locking channel 530 may be within a range from 1 millimeter to 2.5 millimeters. As yet another example, the first axial length D1 of the distal end of each of the at least two clips 310 located outside the locking channel 530 may be within a range from 5.5 millimeters to 7.5 millimeters, and the second axial length D2 of the locking channel 530 may be within a range from 1.5 millimeters to 2 millimeters. The distal ends of the at least two clips 310 located outside the locking channel 530 may be disposed with a sufficient length to clamp the at least one tissue 20, and the locking channel 530 may be disposed with a relatively short length to reduce an overall size of the clip instrument 10.

Figure 25B:
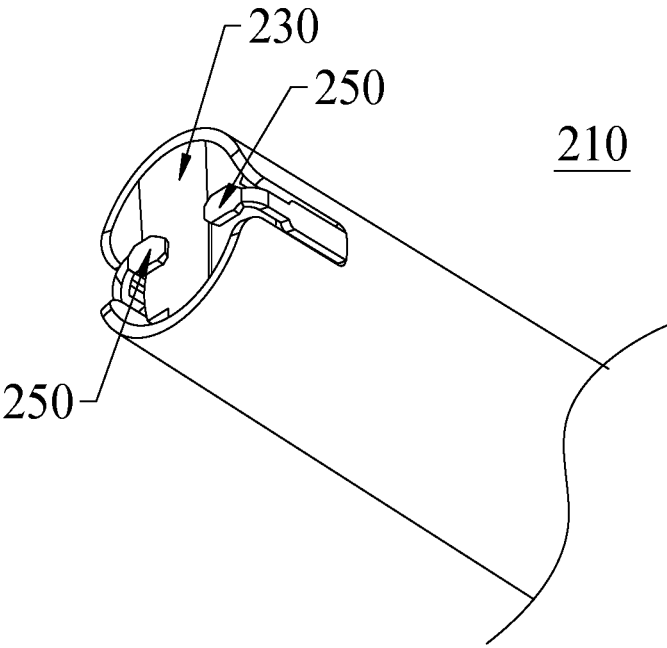
FIG. 25B is a schematic diagram illustrating an exemplary structure of a sheath tube according to some embodiments of the present disclosure.

FIG. 25B is a schematic diagram illustrating an exemplary structure of a sheath tube 210 according to some embodiments of the present disclosure.

As shown in FIGS. 25A and 25B, in some embodiments, the locking part 500 may include at least one first external connecting part 540 (e.g., two first external connecting parts 540 as shown in FIG. 25A), and a distal end of the sheath tube 210 may include at least one second external connecting part 250 (e.g., two second external connecting parts 250 as shown in FIG. 25B). Each of the at least one first external connecting part 540 may be releasably connected to one second external connecting part 250 corresponding to the first external connecting part 540, causing the locking part 500 and the sheath tube 210 to be releasably connected.

In some embodiments, each of the at least one first external connecting part 540 of the locking part 500 may include a connecting groove 541. The connecting groove 541 may be disposed at a proximal end of the locking part

500. A proximal end of the connecting groove 541 may be disposed with an opening 542 that allows the second external connecting part 250 to enter and exit. In some embodiments, each of the at least one second external connecting part 250 of the sheath tube 210 may include at least one hook. The at least one hook may bend inward along a radial direction of the sheath tube 210. In some embodiments, the locking part 500 may be accommodated within the groove 240 of the sheath tube 210, and the at least one hook may engage within the at least one connecting groove 541, thereby connecting the locking part 500 with the sheath tube 210. In some embodiments, when deformation, fracture, or displacement of the at least one hook occurs under a force applied along the direction from the distal end to the proximal end, the at least one hook may separate from the at least one opening 542 of the at least one connecting groove 541, thereby releasing the locking part 500 from the sheath tube 210. In some embodiments, when the at least two clips 310 move along the direction from the distal end to the proximal end, the proximal ends of the at least two clips 310 may abut against the at least one hook and drive the at least one hook to deform, thereby separating from the at least one opening 542 of the at least one connecting groove 541.

In some embodiments, the at least one first external connecting part 540 of the locking part 500 and the at least one first second external connecting part 250 of the sheath tube 210 may also include other structures, as long as the at least one first external connecting part 540 can separate from the at least one first second external connecting part 250 under the force.

In some embodiments, the distal end of the sheath tube 210 may include a resisting part 230, and the proximal end of each of the at least two clips 310 may include a resisted part 320. The distal end of the sheath tube 210 may be disposed with a baffle arranged radially, and the baffle may form the resisting part 230. The proximal end of each of the at least two clips 310 may be bent radially inward to form the resisted part 320. When the core shaft 220 drives each of the at least two extending parts 400 to move along the direction from the distal end to the proximal end, the resisting part 230 and the resisted parts 320 may abut against each other. Each of the at least two extending parts 400 may continue to move along the direction from the distal end to the proximal end, and the resisting part 230 may limit movement of the at least two clips 310 along the direction from the distal end to the proximal end. When the core shaft 220 drives each of the at least two extending parts 400 to move along the direction from the distal end to the proximal end, the resisting part 230 may abut against the distal end of the core shaft 220, limiting the core shaft 220 from moving beyond the distal end of the sheath tube 210, thereby preventing the clip arm 300 from opening excessively.

Figure 26:
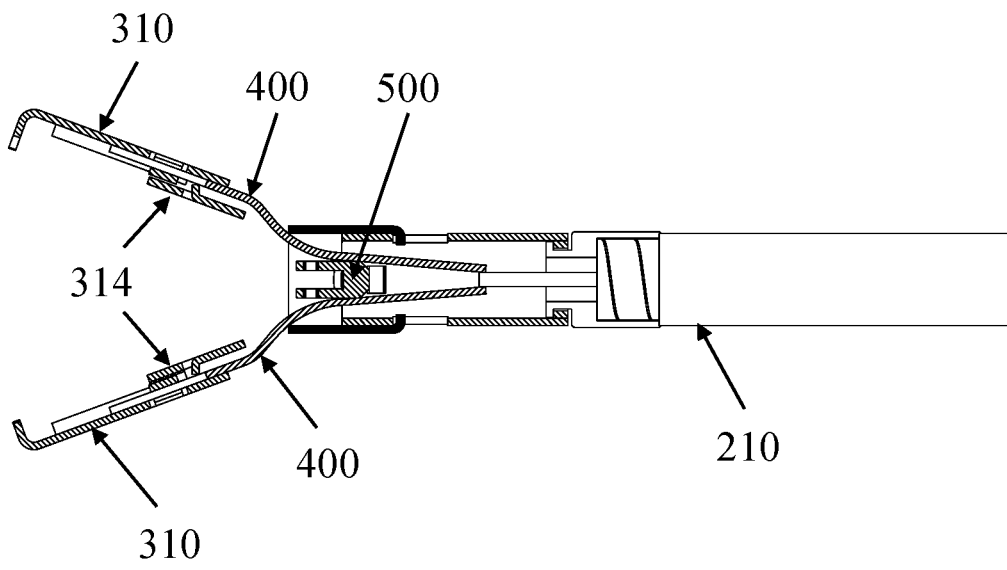
FIG. 26 is a schematic diagram illustrating an exemplary structure of coordination between a locking part and a sheath tube according to some embodiments of the present disclosure.

FIG. 26 is a schematic diagram illustrating an exemplary structure of coordination between a locking part and a sheath tube according to some embodiments of the present disclosure.

As shown in FIG. 26, in some embodiments, the locking part 500 may include a block structure including a locking chamber. The locking part 500 may be releasably disposed within the channel of the sheath tube 210. In some embodiments, the sheath tube 210 may include a clamping seat or other structures. At least a portion of the clamping seat may be disposed within the channel of the sheath tube 210, and the locking part 500 may be releasably disposed on the clamping seat. In some embodiments, the sheath tube 210 or the clamping seat may include a first resisting structure and a second resisting structure. The first resisting structure may cooperate with the proximal end of the locking part 500 to limit the locking part 500 from moving toward the proximal end. The second resisting structure may releasably cooperate with the distal end of the locking part 500 to limit the locking part 500 from moving toward the distal end. In some embodiments, the second resisting structure may be deformed, fractured, or displaced under a force or extrusion, causing the second resisting structure to separate from the locking part 500, thereby releasing the locking part 500 from the sheath tube 210.

In some embodiments, the locking portion 500 may be disposed between the at least two extending parts 400. At least two channels may be formed between the outer side of the locking portion 500 and the inner wall of the sheath tube 210 (or the clamping seat). Each channel may allow that at least one of the at least two extending parts 400 passes through the channel of the sheath tube 210 (or the clamping seat) to the outside of the channel of the sheath tube 210 (or the clamping seat).

In some embodiments, the locking part 500 may cooperate with inner sides of the at least two clips 310. When the at least two clips 310 cooperate with the locking part 500, the locking part 500 may be disposed between the at least two clips 310. A locked part 314 may be disposed inside each of the at least two clips 310. The locking part 500 may be used to form a locking cooperation with the locked parts 314 inside the at least two clips 310. In some embodiments, after the locking part 500 and the at least two clips 310 are locked, the locking part 500 may be located between the at least two clips 310. In some embodiments, the locking part 500 may include at least one stop structure, and the locked parts 314 of the at least two clip 310 may include at least one limiting structure. The at least one stop structure and the at least one limiting structure may match with each other, so that the locking part 500 and the locked parts 314 are locked with each other in any direction.

In some embodiments, the locking part 500 may cooperate with the proximal ends of the at least two clips 310. When the at least two clips 310 cooperate with the locking part 500, a lateral size of the locking part 500 may be less than a lateral size of the at least two clips 310 in the closed state. The lateral size refers to a sectional size perpendicular to a longitudinal direction of the at least two clips 310. In some embodiments, the proximal end of each of the at least two clips 310 may be bent toward the clamping space to form the corresponding locked part 314. The locking portion 500 may be used to form a locking cooperation with the locked parts 314 inside the at least two clips 310.

Figure 27:
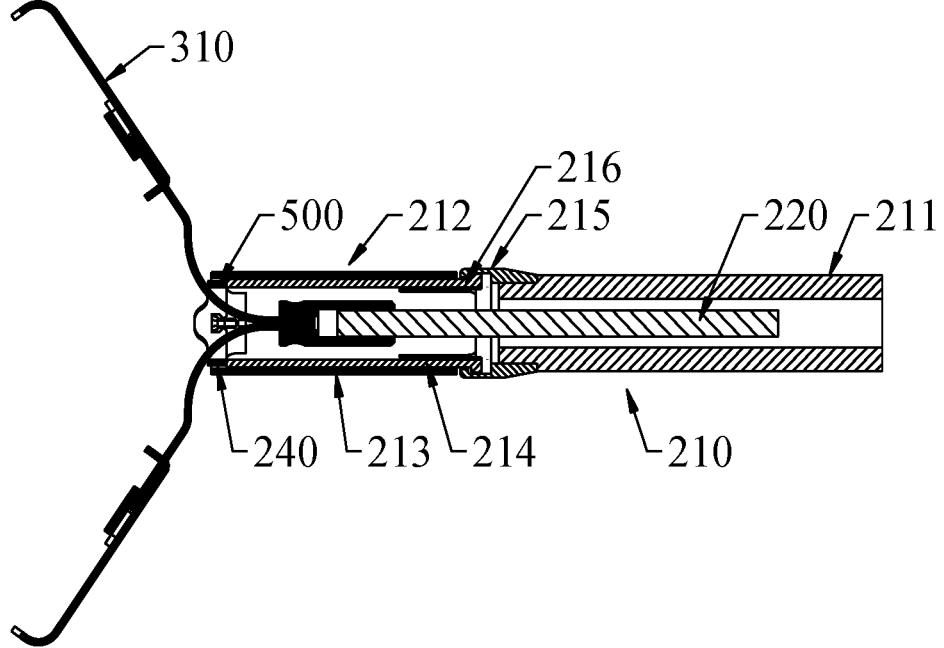
FIG. 27 is a sectional view of a clip arm and a sheath tube according to some embodiments of the present disclosure.

FIG. 27 is a sectional view of a clip arm 300 and a sheath tube 210 according to some embodiments of the present disclosure.

As shown in FIG. 27, in some embodiments, the sheath tube 210 may include a first sheath 211 disposed at a proximal end of the sheath tube 210 and a second sheath 212 connected to the first sheath 211. A channel of the first sheath 211 and a channel of the second sheath 212 may penetrate each other to form a channel of the sheath tube 210. The locking part 500 may be releasably connected to the second sheath 212. The second sheath 212 may be disposed with a groove 240 for accommodating the locking part 500. When the sheath tube 210 is separately formed, the second sheath 212 may facilitate assembly with the at least two clips 310 of the clip arm 300, which is suitable for mass production.

In some embodiments, a distal end of the first sheath 211 may be disposed with a first connecting structure 215, a distal end of the second sheath 212 may be disposed with a second connecting structure 216, and the first connecting structure 215 and the second connecting structure 216 may be detachably connected. In some embodiments, the first connecting structure 215 may include a concave structure, and the second connecting structure 216 may include a convex structure. The concave structure and the convex structure may detachably cooperate with each other to cause the first connecting structure 215 and the second connecting structure 216 to be detachably connected. In some embodiments, the first connecting structure 215 and the second connecting structure 216 may also include other connecting structures.

In some embodiments, the second sheath 212 may include an outer tube 213 and an inner tube 214. Each of the outer tube 213 and the inner tube 214 may be disposed with a channel, and the inner tube 214 may be fixedly disposed within the channel of the outer tube 213. In some embodiments, the groove 240 may be formed by a misaligned combination of a distal end of the outer tube 213 and a distal end of the inner tube 214. Since a size of the second sheath 212 is at the micron level, it may be difficult to form the groove 240 or process within the micron-level channel. Therefore, the outer tube 213 and the inner tube 214 may be assembled to form the groove 240, which can reduce the difficulty of part processing and the processing cost. In some embodiments, a proximal end of the outer tube 213 and a proximal end of the inner tube 214 may also be misaligned to form the first connecting structure 215, thereby reducing the processing difficulty of the first connecting structure 215.

In some embodiments, as shown in FIG. 24, the groove 240 may be formed by processing the distal end of the sheath tube 210, simplifying the overall part.

FIGS. 28 to 31 are schematic diagrams illustrating an exemplary clamping process between at least two clips and at least two extending parts according to some other embodiments of the present disclosure.

Figure 28:
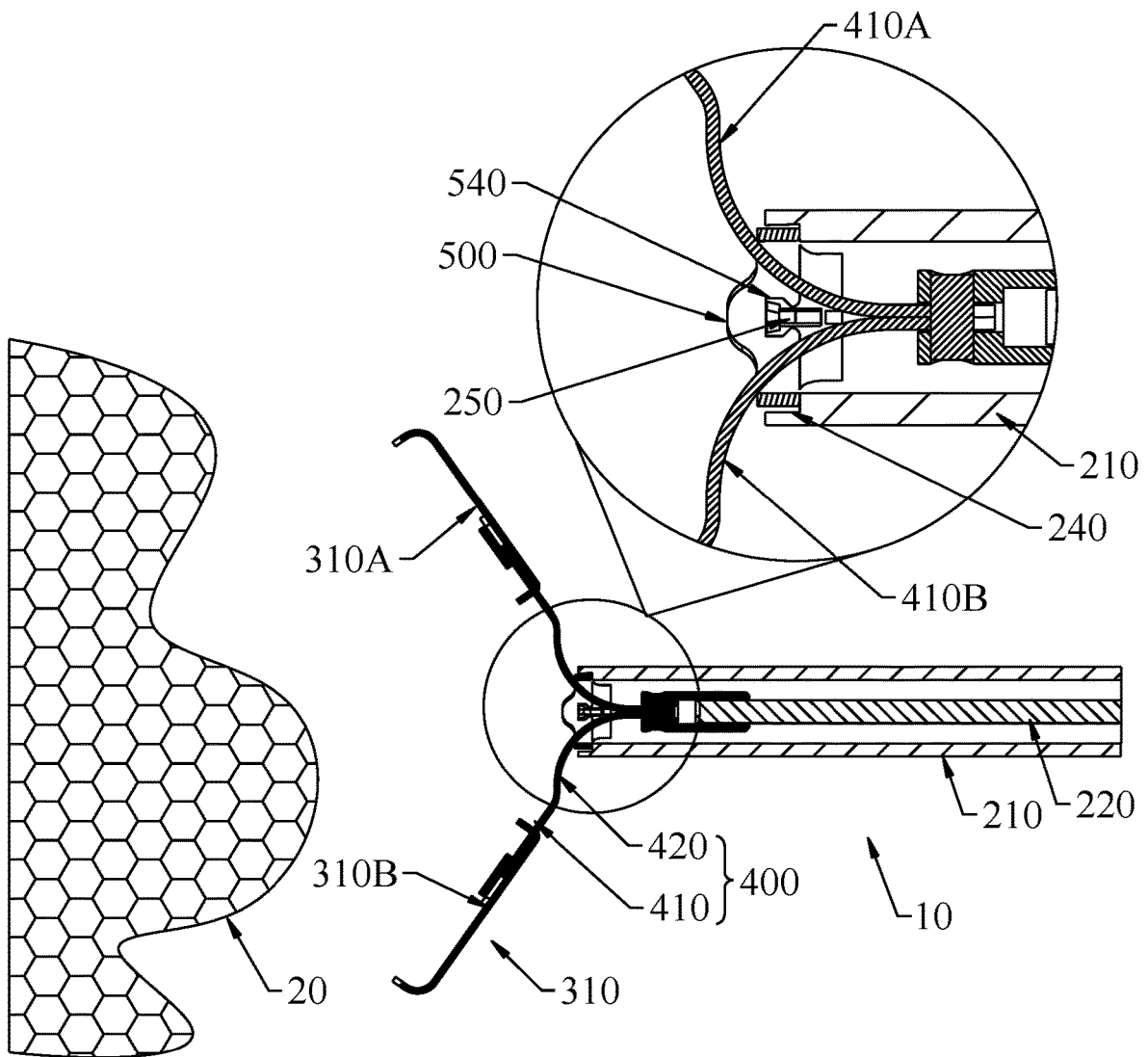
FIGS. 28 to 31 are schematic diagrams illustrating an exemplary clamping process between at least two clips and at least two extending parts according to some other embodiments of the present disclosure.

As shown in FIG. 28, in some embodiments, the clip instrument 10 may be in an open state. The at least two clips 310 and the at least two extending parts 400 may be connected respectively. The core shaft 220 may move axially along the channel of the sheath tube 210 from the proximal end to the distal end. The first extending part 400A and the second extending part 400B accommodated in the channel of the sheath tube 210 may move axially along the direction from the proximal end to the distal end, and cause the distal coupling parts 410 of the first extending part 400A and the second extending part 400B to open under an elastic action of the bending part 420. Therefore, the distal end of the first clip 310A connected to the first extending part 400A and the distal end of the second clip 310B connected to the second extending part 400B may move apart from each other and form a clamping space for receiving the at least one tissue 20. During the opening process of the clip instrument 10, the locking part 500 may be accommodated in the groove 240 at the distal of the sheath tube 210, and the at least one first external connecting part 540 of the locking part 500 may be connected to the at least one second external connecting part 250 of the sheath tube 210.

Figure 29:
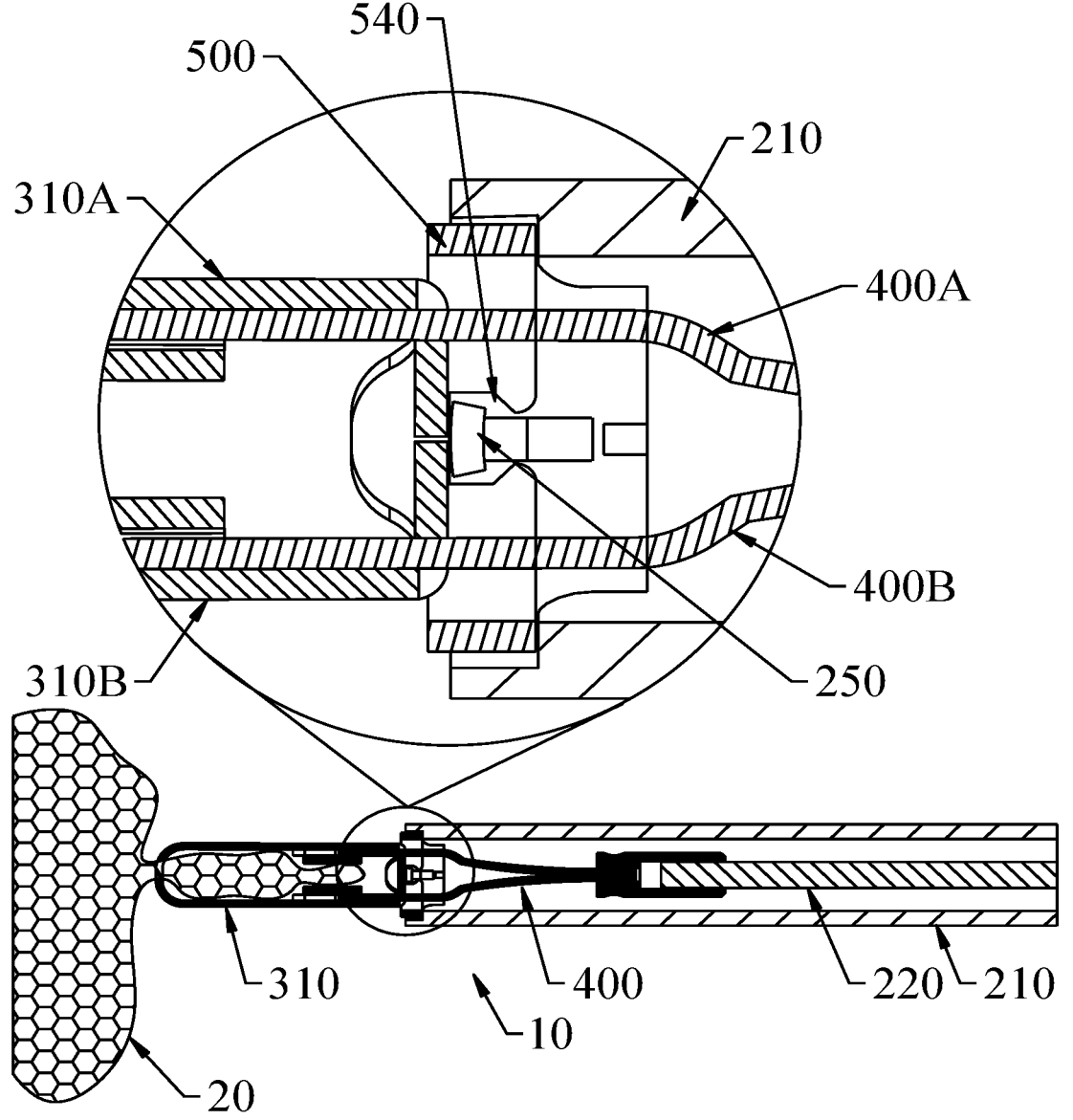

As shown in FIG. 29, in some embodiments, the clip instrument 10 may be in a closed state. The at least two clips 310 and the at least two extending parts 400 may be connected respectively. The core shaft 220 may move axially along the channel of the sheath tube 210 from the distal end to the proximal end. The first extending part 400A and the second extending part 400B may move axially along the direction from the distal end to the proximal end and be accommodated in the channel of the sheath tube 210. The distal coupling parts 410 of the first extending part 400A and the second extending part 400B may approach each other, and the distal ends of the first clip 310A and the second clip 310B may approach each other to clamp the at least one tissue 20. The core shaft 220 may continue to move along the direction from the distal end to the proximal end, and a portion of the at least two clips 310 may not enter the locking part 500. The proximal ends of the at least two clips 310 may abut against the distal end of the at least one second external connecting part 250 of the sheath tube 210. When a force applied to the at least one second external connecting part 250 by the at least two clips 310 is not sufficient to detach the at least one second external connecting part 250 from the at least one first external connecting part 540 of the locking part 500, the at least one second external connecting part 250 may generate a resistance force and feedback to a user. After receiving the feedback resistance, the user may determine a next direction of movement of the core shaft 220 according to a surgical situation. For example, if it is determined that the at least two clips 310 have performed hemostasis, the core shaft 220 may be pulled along the direction from distal end to the proximal end to release the locking part 500 and the sheath tube 210. If it is determined that the at least two clips 310 need to re-clamp the at least one tissue 20, the core shaft 220 may be pushed along the direction from the proximal end to the distal end to reopen the at least two clips 310.

Figures 30, 31:
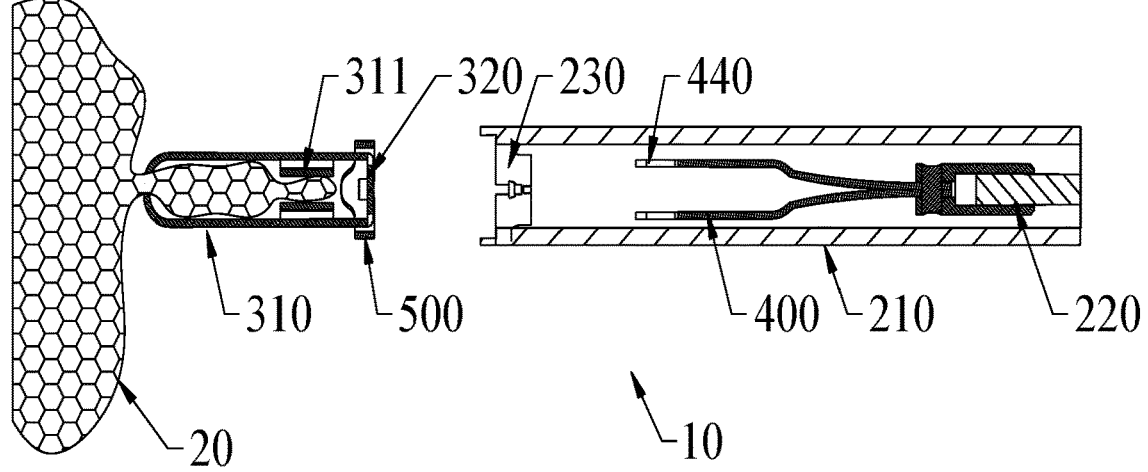

As shown in FIG. 30, in some embodiments, the clip instrument 10 may be in a locked state. After the clip instrument 10 is closed, the core shaft 220 may continue to move axially along the channel of the sheath tube 210 from the distal end to the proximal end. The proximal ends of the at least two clips 310 may push the at least one second external connecting part 250 of the sheath tube 210 to move along the direction from the distal end to the proximal end, causing the second external connecting parts 250 to deform, fracture, or displace and separate from the at least one first external connecting part 540 of the locking part 500, thereby releasing the locking part 500 from the sheath tube 210. Then, each of the at least two clips 310 may move along the direction from the distal end to the proximal end with respect to the locking part 500, the proximal ends of the at least two clips 310 may be accommodated within the locking part 500, and the locked part 314 of each of the at least two clips 310 may cooperate with the locking part 500 (e.g., by interference fit), thus causing the at least two clips 310 to be in the locked state.

As shown in FIG. 31, in some embodiments, the clip instrument 10 may be in a release state. After the clip instrument 10 is locked, the core shaft 220 may continue to move axially along the channel of the sheath tube 210 from the distal end to the proximal end. The at least two extending parts 400 may drive the at least two clips 310 to move along the direction from the distal end to the proximal end, respectively, until the resisted parts 320 of the at least two clips 310 abut against the resisting part 230 of the sheath tube 210, causing the at least two clips 310 to stop moving. Under the tension along the direction from the proximal end to the distal end, the first connecting parts 311 of the at least two clips 310 and/or the second connecting parts 440 of the at least two extending parts 400 may deform, fracture, or displace. The at least two extending parts 400 may be released from the at least two clips 310, and the core shaft 220 may drive the at least two extending parts 400 to remove from the channel of the sheath tube 210. At this time, the at least two clips 310 and the locking part 500 may detach from the groove 240 at the distal end of the sheath tube 210. The at least two extending parts 400, the sheath tube 210, and the conveying part 200 for delivering the sheath tube 210 may be removed from the body, leaving only the at least two clips 310 and the locking part 500 in the body, thereby reducing structures left in the body and minimizing potential risks to the body.

The possible beneficial effects of the embodiments of the present disclosure may include but not limited to the following:

(1) By disposing the locking part on the at least two clips, the at least two clips can be maintained in the closed state within the body, thereby improving the clamping effectiveness of the at least two clips.

(2) By releasably connecting the at least two clips and the at least two extending parts, respectively, the at least two extending parts and the conveying part that are not in contact with the at least one tissue can be removed from the body, and the at least two clips with a relatively small size can be left in the body, which can provide a relatively large operational space for subsequent surgical operation(s) and reduce an impact on the body.

(3) The first length of the locking arm outside the sheath tube when the locking arm is in the open state can be larger than the second length outside the sheath tube when the locking arm is in the closed state, which can improve the span between the at least two clips, and increase the clamping space for holding the at least one tissue, thereby reducing the size of the at least two clips left in the body, and minimizing the impact on the body.

(4) The locking length of the locking part along the extension direction of the clip arm is larger than 1 millimeter to avoid the separation of the distal ends of the at least two clips, which can improve the stability of maintaining the at least two clips in the closed state.

(5) By disposing the locking part close to the proximal ends of the at least two clips, the clamping space for clamping the at least one tissue at the distal ends of the at least two clips can be improved. Additionally, by disposing the locking part away from the location of the at least one tissue, the interference on the cooperation of the locking part can be avoided.

(6) The at least two extending parts can control the clamping of the at least one tissue by opening and closing the first clip and the second clip, and improve the opening span between the first clip and the second clip. The at least two extending parts can be released from the at least two clips, thereby reducing the size of the at least two clips left in the body, and minimizing the impact on the body.

(7) The bending parts of the at least two extending parts may be accommodated in the channel of the sheath tube to save space, and when the bending parts are located outside the channel of the sheath tube, the clipping span between the at least two clips can be improved, which is beneficial to clamp the at least one tissue.

It should be noted that different embodiments may result in different beneficial effects. In different embodiments, the beneficial effects may be any combination of the above or other possible beneficial effects that may be obtained.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A clip instrument, comprising:

a clip arm including at least two clips for clamping at least one tissue and at least two extending parts releasably connected to the at least two clips, respectively, the clip arm having an open state and a closed state, wherein the at least two clips are spaced apart from each other when the clip arm is in the open state, and the at least two clips are close to each other when the clip arm is in the closed state;

a locking part disposed on the at least two clips, wherein the locking part is configured to lock two clips of the at least two clips when a distance between the two clips is less than a preset distance; and a conveying part including a sheath tube disposed with a channel and a core shaft axially extending along an axial direction within the channel of the sheath tube, a distal end of the sheath tube including a resisting part, wherein for each of the at least two extending parts, a proximal end of the extending part is connected to the core shaft, a distal end of the extending part is releasably connected to one of the at least two clips corresponding to the extending part, an axial movement of the at least two extending parts drives the clip arm to switch between the open state and the closed state, and the proximal end of each of the at least two extending parts is disposed with a resisted part;

after the at least two clips are locked, when each of the at least two extending parts continues to move along a direction from the distal end of the extending part to the proximal end of the extending part, the at least two extending parts are released from the at least two clips, and the clip arm is released from the sheath tube;

after the resisting part and the resisted part abut against each other, when each of the at least two extending parts continues to move along the direction from the distal end of the extending part to the proximal end of the extending part, the resisting part limits movement of the resisted part along the direction from the distal end of the extending part to the proximal end of the extending part.

2. The clip instrument of claim 1, wherein a locking length of the locking part along an extension direction of each of the at least two clips is not less than 1 millimeter.

3. The clip instrument of claim 1, wherein proximal ends and distal ends of the at least two clips are closed when the clip arm is in the closed state.

4. The clip instrument of claim 1, wherein for each of the at least two clips, a ratio of a distance between a distal end of the locking part and a distal end of the clip to a distance between the distal end of the locking part to a proximal end of the clip is larger than 1.

5. The clip instrument of claim 1, wherein the at least two clips include a first clip and a second clip, and the locking part includes a first locking part disposed on the first clip and a second locking part disposed on the second clip; and the locking part has an unlocked state and a locked state, wherein the first locking part and the second locking part separate from each other when the locking part is in the unlocked state, and the first locking part and the second locking part cooperate with each other to lock the first clip and the second clip when the locking part is in the locked state.

6. The clip instrument of claim 5, wherein the first locking part includes at least one locking protrusion, and the second locking part includes at least one locking recess, wherein each of the at least one locking protrusion and one of the at least one locking recess corresponding to the locking protrusion cooperate with each other to lock the first clip and the second clip.

7. The clip instrument of claim 6, wherein the first locking part is integrally formed with the first clip, the first locking part being formed at a proximal end of the first clip, and the second locking part is integrally formed with the second clip, the second locking part being formed at a proximal end of the second clip.

8. The clip instrument of claim 1, wherein a first length of the clip arm outside the sheath tube in the open state is larger than a second length outside the sheath tube in the closed state.

9. The clip instrument of claim 1, wherein the at least two clips include a first clip and a second clip, and the at least two extending parts include a first extending part and a second extending part, wherein a proximal end of the first extending part and a proximal end of the second extending part are connected to the core shaft, a distal end of the first extending part is releasably connected to the first clip, and a distal end of the second extending part is releasably connected to the second clip.

10. The clip instrument of claim 9, wherein each of the first extending part and the second extending part is disposed with a distal coupling part, a bending part, and a proximal coupling part, wherein the distal coupling part is releasably connected to one of the at least two clips, the bending part is connected to the distal coupling part and the proximal coupling part, and the proximal coupling part is connected to the core shaft; and the bending part has elasticity, such that the bending part causes the distal coupling part of the first extending part and the distal coupling part of the second extending part to move away from each other when the clip arm is in the open state, and the bending part deforms to provide a locking force for the locking part when the clip arm is in the closed state.

11. The clip instrument of claim 10, wherein when the clip arm is in the open state, a bending angle of the bending part is within a range from 30 degrees to 130 degrees.

12. The clip instrument of claim 10, wherein when the clip arm is in the open state, an angle between the distal coupling part and a section at a connection of the distal coupling part and the bending part is within a range from 95 degrees to 115 degrees.

13. The clip instrument of claim 1, wherein each of the at least two clips is disposed with a first connecting part, and the distal end of each of the at least two extending parts is disposed with a second connecting part, wherein the first connecting part and the corresponding second connecting part cooperate with each other to cause the clip to be releasably connected to the extending part.

14. The clip instrument of claim 13, wherein when deformation, fracture, or displacement of at least one of the first connecting part or the second connecting part occurs under a force, the at least two extending parts are released from the at least two clips, respectively.

15. The clip instrument of claim 14, wherein the first connecting part includes a limiting channel, and a distal end of the second connecting part is disposed with at least one limiting protrusion, wherein the second connecting part is inserted into the limiting channel, and the at least one limiting protrusion protrudes from a distal end of the limiting channel and is releasably clamped with the limiting channel.

16. The clip instrument of claim 14, wherein the first connecting part includes a shrapnel protruding radially inward, and the second connecting part includes a limit buckle, wherein the limit buckle is releasably clamped with the shrapnel.

17. The clip instrument of claim 1, wherein the sheath tube includes a first sheath disposed at a proximal end of the sheath tube and a second sheath connected to the first sheath, a channel of the first sheath and a channel of the second sheath penetrating each other to form the channel of the sheath tube; wherein a distal end of the first sheath is disposed with a first connecting structure, a distal end of the second sheath is disposed with a second connecting structure, and the first connecting structure and the second connecting structure are detachably connected.

\* \* \* \* \*